United States Patent [19]

Bledsoe

[11] Patent Number: 4,817,588
[45] Date of Patent: Apr. 4, 1989

[54] MOTION RESTRAINING KNEE BRACE

[75] Inventor: Gary R. Bledsoe, Grand Prairie, Tex.

[73] Assignee: Medical Technology, Inc., Grand Prairie, Tex.

[21] Appl. No.: 68,931

[22] Filed: Jul. 1, 1987

[51] Int. Cl.⁴ .............................................. A61F 5/00
[52] U.S. Cl. .................................. 128/80 C; 128/80 F
[58] Field of Search ...................... 128/80 C, 80 F, 88

[56] References Cited

U.S. PATENT DOCUMENTS

| | | | |
|---|---|---|---|
| 21,872 | 10/1859 | Bunce | 128/88 |
| 552,143 | 12/1895 | Ranklin | 128/80 F |
| 2,250,493 | 7/1941 | Milne | 128/77 |
| 2,558,986 | 7/1951 | Seelert | 128/80 F |
| 3,785,371 | 1/1974 | Lew/ | 128/77 |
| 3,805,773 | 4/1974 | Sichaw | 128/80 F |
| 4,057,056 | 11/1977 | Payton | 128/83.5 |
| 4,057,853 | 11/1977 | McLane | 2/22 |
| 4,090,508 | 5/1978 | Gaylord, Jr. | 128/80 |
| 4,240,414 | 12/1980 | Theisler | 128/80 |
| 4,271,831 | 6/1981 | Deibert | 178/80 C |
| 4,337,764 | 7/1982 | Lerman | 128/80 F |
| 4,340,041 | 7/1982 | Frank | 128/80 |
| 4,381,768 | 5/1983 | Errehson et al. | 128/80 C |
| 4,463,751 | 8/1984 | Bledsoe | 128/88 |
| 4,531,731 | 7/1985 | Law | 272/145 |
| 4,554,913 | 11/1985 | Womack et al. | 128/80 |
| 4,556,053 | 12/1985 | Irons | 128/88 |
| 4,565,190 | 1/1986 | Pirmantgen et al. | 128/80 C |
| 4,572,170 | 2/1986 | Cronk et al. | 128/80 |
| 4,614,181 | 9/1986 | Karlsson | 128/80 |
| 4,620,532 | 11/1986 | Houswerth | 128/80 F |
| 4,624,247 | 11/1986 | Ford | 128/80 C |
| 4,632,098 | 12/1986 | Grandei et al. | 128/80 C |
| 4,633,867 | 1/1987 | Kausek et al. | 128/88 |
| 4,649,906 | 3/1987 | Spademan | 128/80 |

FOREIGN PATENT DOCUMENTS

| | | | |
|---|---|---|---|
| 170739 | 5/1906 | Fed. Rep. of Germany | 128/88 |
| 1024204 | 2/1958 | Fed. Rep. of Germany | 128/80 C |
| 8502536 | 6/1985 | PCT Int'l Appl. | 128/80 F |
| 110209 | 10/1917 | United Kingdom | 128/88 |
| 1449554 | 9/1976 | United Kingdom | 128/80 F |

Primary Examiner—Edgar S. Burr
Assistant Examiner—Tonya Lamb
Attorney, Agent, or Firm—Hubbard, Thurman, Turner & Tucker

[57] ABSTRACT

A motion restraining knee brace has a pair of articulated side portions each defined by elongated thigh and calf support members pivotally interconnected by an adjustable hinge mechanism. Each hinge mechanism has a single adjustment dial that cooperates with a pair of stop members to selectively limit the relative pivotal movement between the thigh and calf support members associated with the hinge. Outer ends of the thigh and calf support members are securable to the leg by connecting straps which encircle the leg and have independently adjustable anterior and posterior portions. Each of the thigh and calf support members is formed from two adjustably interlockable longitudinal sections releasably held together by a pivotable clip member to thereby provide for rapid support member length adjustment. To inhibit extension of the leg beyond the hingeestablished extension limit angle of the brace, a restraining strap member is looped through eyed connectors carried by each of the support members to form a generally hourglass-shaped strap network positioned behind the knee. As the leg is extended, the strap network is progressively tightened against it, with each portion of the network being held in essentially equal tension, to inhibit overextension of the leg.

38 Claims, 6 Drawing Sheets

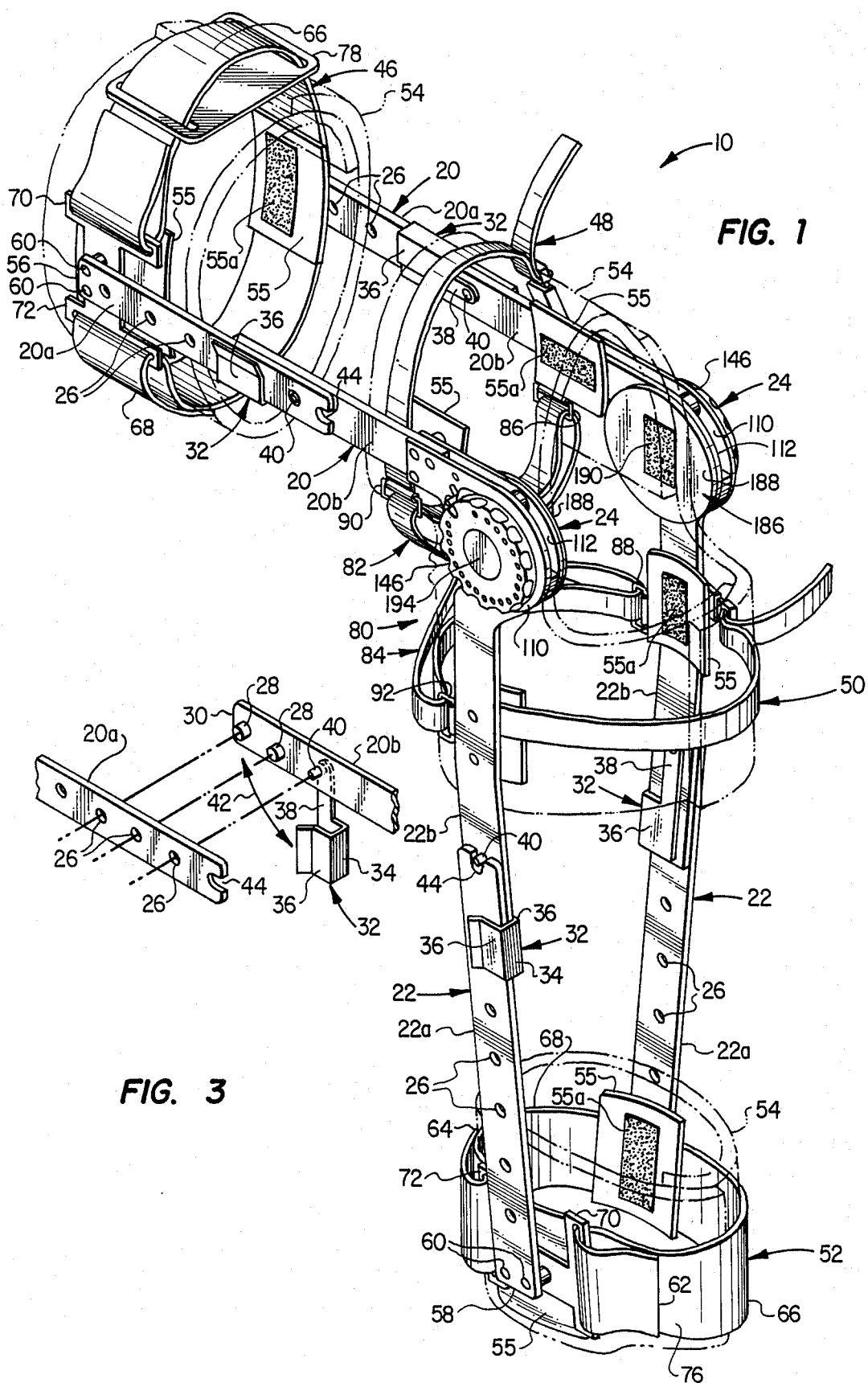

MOTION RESTRAINING KNEE BRACE

BACKGROUND OF THE INVENTION

The present invention relates generally to orthopedic appliances, and more particularly provides a uniquely constructed motion restraining knee brace incorporating a variety of improvements over conventional knee braces of this general type.

Following various types of knee injury or surgery, it is often necessary to restrict the pivotal motion of the knee joint to a predetermined angular range extending between an extension limit angle and a flexion limit angle while the knee heals. This pivotal restraint is typically accomplished by securing to the leg a motion restraining knee brace having a pair of articulated side portions positionable on opposite lateral sides of the leg. Each of these side portions is conventionally defined by elongated thigh and calf support members which are pivotally connected at inner ends portions thereof by an adjustable hinge mechanism which is positionable to one side of the knee with its interconnected thigh and calf support members respectively extending longitudinally along thigh and calf portions of the leg on the same lateral side thereof.

The two thigh support members, and the two calf support members, are secured to their associated leg portions by various strap and cushioning pad members which encircle the leg and may be adjustably tightened or loosened against it to hold the support members firmly in place on the leg. The two hinge mechanisms are typically adjustable to selectively limit the relative pivotal motion between the interconnected support members on opposite sides of the leg to thereby limit the pivotal motion of the healing knee to a predetermined angular range extending between an extension limit angle and a flexion limit angle. Thus, for example, if it is medically necessary to restrict the movement of the knee to a pivotal range extending between a 30° flexion angle and a 90° flexion angle, the hinge mechanisms are simply adjusted to limit the relative pivotal motion of each of the interconnected support member sets to this range.

While conventional knee braces of this general type have proven to be quite beneficial in protecting knee joints following injury thereto or surgery thereon, it is well known that such knee braces are subject to a variety of problems, limitations and disadvantages. For example, one such limitation or disadvantage is associated with the need to adjust the overall length of the brace's thigh and/or calf support members to accommodate legs of varying lengths. To solve this adjustment problem, some brace manufacturers simply fabricate their knee braces with thigh and calf support members of varying fixed lengths, and a particular brace size must be selected to generally fit a given leg.

In other conventional knee braces, each of the thigh and calf support members is formed from two adjustably interconnectable longitudinal sections which may be intersecured in selectively variable positions to thereby alter the length of each of the four support members. This adjustment scheme renders it possible to use a single knee brace on legs of varying lengths. However, the interconnection between the two longitudinal sections of each of the support members has heretofore been somewhat awkward and laborious to adjust and has been prone to undesirable slippage. This is particularly true when the two associated support member sections are clamped together or otherwise frictionally engaged with one another. Various removable locking members have also been utilized to provide a more secure interconnection between the two sections, but such locking members are prone to loosening and dislodgment during use of the brace which can result in damage to the knee when the brace subsequently fails to properly restrain its pivotal motion.

Another limitation inherent in conventional knee braces of this general type is associated with the connection of the thigh and calf support members to the leg. Such connection is typically accomplished by connecting straps which are secured to the thigh support and calf support member pairs and are adapted to be looped entirely around the leg and then tightened to securely hold the support members against the leg. With this connection strap structure, however, it is somewhat difficult to properly align the support members in an anterior-posterior sense relative to the particular leg portions along which they extend. More specifically, the use of conventional connecting straps requires that each pair of thigh or calf support members be manually held in proper anterior-posterior alignment with the leg while their connecting strap is looped around the leg and then tightened. If this connection process is not carefully and skillfully performed, one or more of the four support members may be undesirably misaligned with lateral side portions of the leg after the brace has been secured thereto.

Another disadvantage commonly associated with conventional motion restraining knee braces is the difficulty encountered in preventing the leg from being pivotally extended beyond the extension limit angle setting of the brace. Specifically, despite the fact that the interconnected support member sets positioned on opposite lateral sides of the leg are securely strapped thereto, and may pivot only between the angular limits set by their associated hinge mechanisms, the leg itself (because of soft tissue "give") may often be extended somewhat past the extension limit angle setting of the brace. This, of course, to some extent defeats the purpose of the brace.

One solution to this over-extension problem, of course, is to simply set the extension limit of the brace somewhat less than the desired extension limit of the leg to thereby compensate for this soft tissue give. This solution, though, is at best a trial-and-error procedure which must be carefully and skillfully performed because of the variance in soft tissue characteristics among different legs.

Another proposed solution to this over-extension problem has been to provide the brace with a single posterior restraining strap which is interconnected between the side portions of the brace and positioned directly behind the knee joint. By appropriately tightening this restraining strap against the back of the knee, the patient's ability to extend the leg beyond the extension limit setting of the brace is substantially reduced. However, the positioning of the single restraining strap in this manner has proven to be a source of considerable patient discomfort since, as the leg is flexed, the strap interferes with flexion of the leg.

A further proposed solution has been to eliminate the single restraining strap and replace it with two posterior restraining straps respectively positioned longitudinally above and longitudinally below the knee joint. These two straps are designed to provide the extension-restraining function of the single central strap without the patient discomfort associated therewith. However, by moving the two straps away from the knee joint itself, their extension-inhibiting action is significantly diminished. Additionally, it is well known that the extension strength of the human leg progressively increases as the leg approaches its fully extended position. This presents the problem of determining just how much each of these two restraining straps should be tightened against the leg. Specifically, if they are tightened sufficiently to suitably restrain the leg as it approaches the extension limit angle setting of the brace, they will be too tight when the leg is in other positions within the angular setting of the brace.

Finally, the hinge mechanisms of conventional motion restraining knee braces typically present a variety of difficulties in their adjustment and/or their ability to strongly and reliably maintain their angular limit settings. As an example, various conventional hinge mechanisms utilize removable locking pin elements to define angular stops which limit the pivotal motion of one of the support members associated with the hinge. Other conventional hinges utilize various types of movably supported elements which define pivotal stop surfaces for one of the support members. The adjustment of conventional hinge mechanism of this and other types tend to be somewhat cumbersome and time-consuming. Additionally, the possibility exists that the various locking members may be dislodged and lost, or jarred out of position, which can result in hinge malfunction and possible damage to the leg.

From the foregoing it can be seen that conventional motion restraining knee braces are subject to a variety of problems, limitations and disadvantages. It is accordingly an object of the present invention to provide an improved motion restraining knee brace which eliminates or minimizes above-mentioned and other problems, limitations and disadvantages typically associated with such conventional knee braces.

SUMMARY OF THE INVENTION

In carrying out principles of the present invention, in accordance with a preferred embodiment thereof, a significantly improved motion restraining knee brace is provided which includes a pair of articulated side portions positionable on opposite lateral sides of a human leg. Each of the side portions is defined by elongated, rigid thigh and calf support members which are respectively positionable to extend longitudinally along thigh and calf portions of the leg. These support members are preferably of a metal, plate-like construction and are pivotally interconnected, at facing end portions thereof, by an adjustable locking hinge mechanism which is positionable to one side of the knee. The hinge mechanism may be rapidly and easily adjusted to limit the relative pivotal motion of the interconnected thigh and calf support members to a predetermined angular range extending between a selectively variable leg extension limit angle and a selectively variable leg flexion limit angle. Connecting strap means are provided to firmly secure the brace side portions to the leg to thereby limit the pivotal motion thereof, about the knee, to the predetermined angular range setting of the hinge mechanisms.

According to a feature of the present invention, each of the elongated thigh and calf support members is formed from overlapping, interlockable inner and outer longitudinal sections. One of these sections has formed therethrough a longitudinally spaced series of openings, each adjacent pair of which is adapted to laterally receive a spaced pair of protruberances formed on the other section to create a pivotal and translational shear lock connection between the two sections. To prevent the lateral separation of the two interlocked sections a generally U-shaped clip member is secured to one of the sections for pivotal movement between a first position in which lateral separation of the interlocked sections is permitted, and a second position in which opposite transverse leg portions of the clip member overlie and engage outer surfaces of an overlapping portion of the interlocked sections to prevent such lateral separation.

The overall length of the particular support member may be rapidly and easily adjusted simply by moving the restraining clip member to its first position, laterally separating the interlocked support member sections, inserting the lateral protruberances on one of the sections into a new pair of openings in the other section, and then pivoting the clip member to its second or restraining position. The interlocked protruberances and openings in the two sections, and the resulting shear lock therebetween, firmly holds the support member in its newly adjusted position until a further length adjustment is desired.

In accordance with another aspect of the present invention, the connecting strap means include a pair of connecting straps having central portions. One of these central portions is anchored to an outer end of one of the thigh support members, while the other central strap portion is anchored to an outer end of one of the calf support members. At the outer ends of the other thigh and calf support members are secured a pair of slotted connector elements. The free end portions of each of the connecting straps is looped through one of the slotted connector elements and then secured to itself so that each of the two connecting straps thereby has defined thereon independently adjustable anterior and posterior portions.

This feature significantly facilitates the precise anterior-posterior alignment of the support members along the thigh and calf portion of the leg. Specifically, all that is necessary to rapidly and precisely obtain this support member alignment is to appropriately tighten or loosen one of the anterior and posterior strap portions until its associated support member is positioned in proper alignment on the leg against the restraining force of the adjusted anterior or posterior strap portion. The other adjustable portion of the particular connecting strap is then connected to itself and suitable tightened to maintain the predetermined support member-leg relative alignment.

The conventional problem of extension of the leg past the extension limit angle of the brace is uniquely solved in the present invention by its provision of a criss-crossed restraining strap network which is carried by the brace support members posteriorily of the leg. In a preferred embodiment thereof, the restraining strap network comprises two restraining straps which are slidably looped through two slotted connector elements carried by the thigh support members above the knee, and two connector elements carried by the calf support members below the knee, and then buckled to each other to form a generally hourglass-shaped strap network having first and second end portions joined by a criss-crossed central strap portion. The first strap end portion extends transversely around a posterior portion of the leg positioned above the knee, while the second strap end portion extends transversely around a posterior portion of the leg positioned below the knee. The criss-crossed central portion of the strap network is positioned directly behind the knee.

As the leg is extended toward its extension limit, as determined by the settings of the adjustable hinge mechanisms, the restraining strap network is progressively tightened against the back of the leg, the tightness of the network reaching a maximum level as the leg reaches its brace-determined extension limit angle. This unique strap network exerts an extension inhibiting force against the back of the leg which compensates for soft tissue "give" and prevents appreciable extension of the leg past the extension limit angle therefor.

Importantly, the anteriorily directed restraining force of the strap network closely tracks the available extension power of the leg which, as is well known, progressively increases as the leg is pivoted towards its fully extended position. Additionally, because the two restraining straps are slidably looped through the four connector elements carried by the support member portions of the brace, the tension in each section of the criss-crossed restraining strap network—namely, the two end portions and the crossed central portion—are kept in essentially equal, progressively increasing states of tension as the leg is moved towards its extension limit position. This, of course, maintains a constant level of tightness along the entire length and width of the restraining strap network to firmly, yet comfortably inhibit overextension of the leg.

The adjustable locking hinge mechanisms of the present invention are specially designed and constructed to permit rapid and easy adjustment of both the extension and flexion limit angle settings of the brace. Each of these adjustable hinge mechanisms comprises a pair of laterally spaced, generally circularly shaped base plates, each of which has formed therein circumferentially spaced arcuate extension and flexion slots adjacent their peripheries. Each of the slots, around a radially inner portion thereof has formed therein a circumferentially spaced series of notches, while the radially outer portion of the slots are essentially unobstructed. The inner end of one of the thigh support members is positioned between and anchored to these support plates. The inner end of one of the calf support members is positioned between and pivotally connected to the base plates by means of a pivot pin member which also secures a dial element to an outer side surface of one of the base plates for rotation relative thereto.

Sandwiched between the two base plates are an extension pivot stop disc and a flexion pivot stop disc, each of which is provided with a central locking pin that projects axially outwardly from opposite sides of its associated disc. Opposite ends of the locking pin portion of the extension stop disc are carried in the two extension slots, while opposite ends of the locking pin portion of the flexion stop disc are carried in the flexion slots. An annular flange portion of the dial member functions to captively retain these pin portions in predetermined circumferentially aligned pairs of the notches in the extension and flexion slots to thereby lock the extension and flexion stop discs against circumferential movement around their associated base plate slots.

Circumferentially locked in this manner relative to the base plates, the extension and flexion discs define stop members which are engageable by curved stop surfaces formed on the inner end of the calf support member to thereby limit its pivotal motion relative to the base plates. In turn, this establishes and maintains the relative pivotal motion between the interconnected thigh and calf support members. Specifically, when the extension stop surface on the calf support member engages the circumferentially locked extension stop disc, the thigh and calf support members are at the extension limit angle for the hinge mechanism. Similarly, when the flexion stop surface of the calf support member is brought into engagement with the flexion stop disc, the thigh and calf support members are at the flexion limit angle of the hinge mechanism.

The relative circumferential orientation of the two locking discs may be rapidly and easily changed simply by rotating the dial member. During an initial rotational movement of the dial, a spring member carried thereby engages one of the locking pin portions of the stop discs and urges it radially outwardly from its slot retaining notches into a radial depression formed in the inner surface of the annular dial flange, thereby outwardly shifting the disc. The dial may then be further rotated to bring the shifted disc into alignment with another pair of notches in its associated slots, the spring member holding the locking pin in the flange depression during this subsequent rotation of the dial to thereby move the pin circumferentially with the dial. When the disc pin is urged outwardly from its initial slot notch pair, a portion of the disc is moved outwardly of the aligned peripheries of the base plates.

After the outwardly shifted disc pin has been moved into alignment wit a new pair of slot notches, its disc may be manually pushed toward the new slot pair to move the locking pin out of the dial flange depression and into the new notch pair. While the disc is manually held in its inwardly shifted position, the dial is rotated again so that the dial flange engages the inwardly shifted pin and captively retains it in its new pair of slot notches to thereby lock the moved disc in its new circumferential position relative to the base plates. The dial may then be used to similarly reposition the other locking disc (if desired) to thereby alter the pivotal angular range of the hinge mechanism and both the extension and flexion limit angle settings thereof.

A dial locking disc is also sandwiched between the two base plates and has a central pin portion the opposite ends of which are captively retained in an aligned pair of radially extending slots formed through each of the base plates. The exterior periphery of the dial is provided with a pair of radially projecting, generally triangularly shaped tabs which define therebetween a V-shaped notch. Movement of either of these triangular dial tabs past the dial locking disc forces the pin portion thereof radially outwardly along its retaining slots. The pin portion of the dial locking disc is spring-biased in a radially inward direction relative to the base plates so that when the pin portion is forced outwardly by one of the triangular dial tabs, and the dial is further rotated, an outer end portion of the dial locking disc pin is popped into the V-shaped exterior dial notch. The spring biased pin of the dial locking disc in this position inhibits rotation in either direction of the dial so that once the extension and flexion limit discs are appropriately locked in predetermined circumferential positions thereof, the dial flange retains the two discs in their adjusted position and prevents their pin portions from escaping from the slot notches.

To prevent (or at least significantly inhibit) patient tampering with the limit stop settings of the hinge mechanism, a pair of aligned openings are formed through the base member adjacent the radial slots which carry the pin portion of the dial locking disc. A plastic locking tie member is provided which may be inserted through these openings and then locked to itself. The tie member is positioned to prevent radial outward movement of dial locking disc. Thus, with the locking disc positioned in the V-shaped exterior notch on the dial, and the locking tie in place, the dial cannot be turned in either direction, and patient alteration of the flexion and extension limit angles of the hinge mechanism cannot be effected without cutting and removing the locking tie.

Importantly, each of the locking hinge mechanisms may be rapidly adjusted without the use of tools of any sort, and have no components which may be dislodged and lost. All of the adjustment components of such hinge mechanism are conveniently and captively retained on the base plate portions thereof. The interlocking slots and disc pins provide a very strong and secure shear lock therebetween which positively limits the relative pivotal motion between the interconnected thigh and calf support members to a predetermined pivotal angular range extending between the aforementioned extension and flexion limit angles. The hinge mechanisms are of quite simple, yet very rugged construction and are relatively inexpensive to produce.

From the foregoing it can be seen that the present invention provides a motion restraining knee brace which uniquely eliminates or minimizes a variety of problems, limitations and disadvantages heretofor associated with conventional knee brace apparatus of this general type. The lengths of each of the thigh and calf support members are more easily and securely adjustable, the independent anterior and posterior adjustment capabilities of the support member connecting straps provide for more precise alignment between the support members and the leg to which the brace is connected, and the criss-crossed restraining strap network substantially eliminates the problem of potential leg over extension in a very simple yet quite effective manner. Coupled with the rapidly and securely adjustable locking hinge mechanisms just described, these three features of the present invention are seen to constitute a significant improvement in the knee brace art.

BRIEF DESCRIPTION OF THE DRAWINGS

FIG. 1 is a perspective view of an adjustable, motion restraining knee brace that embodies principles of the present invention;

FIG. 3 is an exploded, fragmentary perspective view of a central portion of one of the two thigh support members of the brace and illustrates a unique, rapid length adjustment feature thereof;

FIGS. 11A—13A are cross-sectional views through the hinge assembly, similar to FIG. 9A and 9B, and sequentially illustrate the position of the pivot stop member during each of the adjustment steps depicted in FIGS. 11-13.

DETAILED DESCRIPTION

Figure 2A:
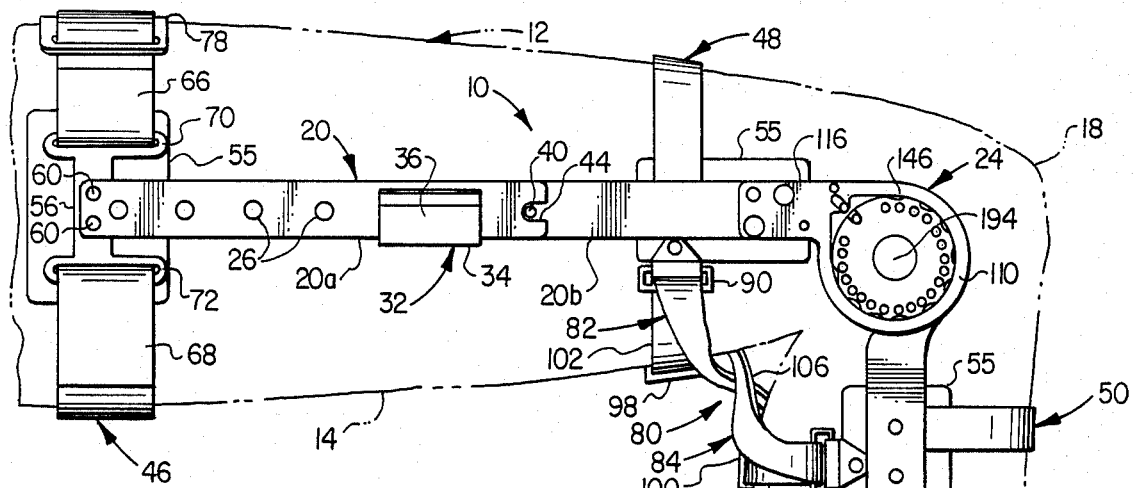
FIGS. 2A and 2B are side views of the brace operatively connected to a portion of a human leg, illustrated in phantom, and limiting pivotal motion of the leg, about the knee, to an angular range extending between a flexion limit angle depicted in FIG. 2A and an extension limit angle depicted in FIG. 2B.
Figure 2B:
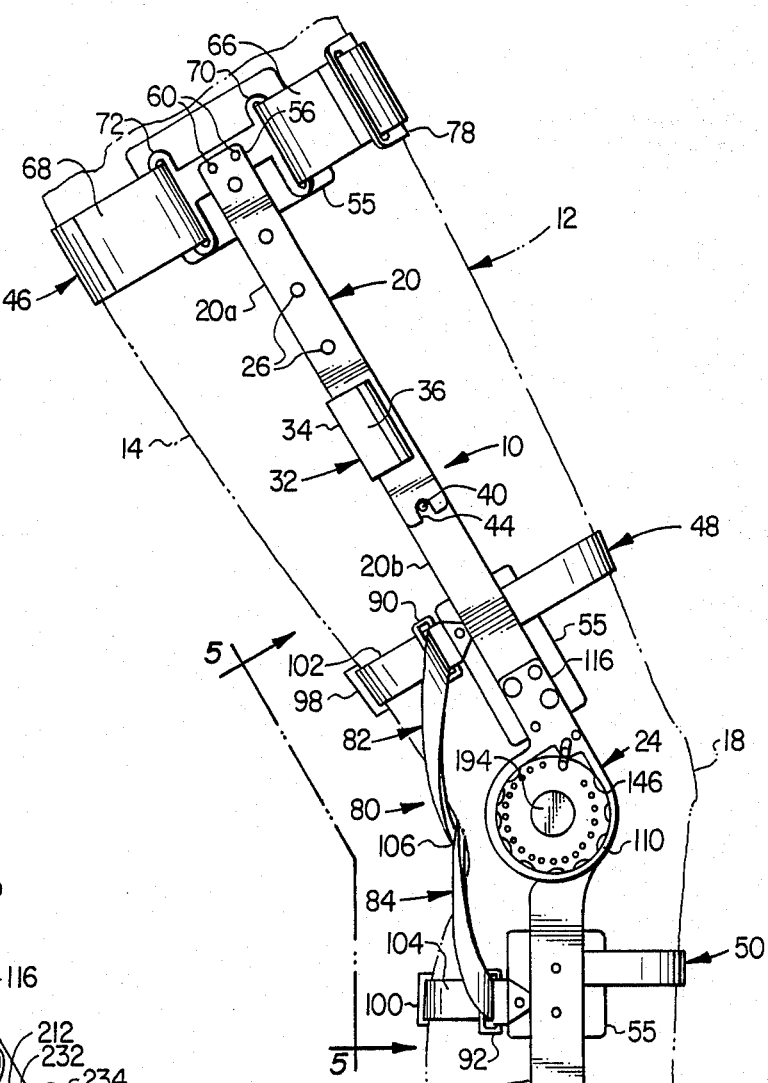

Referring first to FIGS. 1, 2A and 2B, the present invention provides an improved motion restraining leg brace 10 which is connectable to a human leg 12 having a thigh portion 14, a calf portion 16, and a knee 18, and is operative to limit the pivotal extension and flexion motion of the leg about the knee. Brace 10 includes a pair of elongated, rigid thigh support members 20 positionable to extend longitudinally along opposite lateral sides of the thigh portion 14, and a pair of elongated, rigid calf support members 22 positionable to extend longitudinally along opposite lateral sides of the calf portion 16. Thigh and calf support members 20, 22 are preferably of a flat metal plate construction. They could, however, be alternately formed from another suitably rigid material having a different cross-section if desired.

The thigh and calf support member sets 20, 22 positioned on opposite sides of the leg 12 are pivotally interconnected at their facing inner ends by a pair of specially designed adjustable locking hinge mechanisms 24 which are positionable on opposite lateral sides of the knee 18. In a manner subsequently described, each of the hinge mechanisms 24 may be rapidly and easily adjusted to selectively limit the relative pivotal motion between the support members 20, 22 in each set thereof (and thus the pivotal motion of the leg 12) to a predetermined angular range extending between a selectively variable flexion limit angle (FIG. 2A) and a selectively variable extension limit angle (FIG. 2B). For purposes of illustration, the hinges 24 in FIGS. 1, 2A and 2B have each been shown with a representative 90° flexion limit angle setting and a representative 30° extension limit angle. Accordingly, with the brace 10 operatively secured to the leg 10, the leg may be pivoted only between flexion angles of 90° (FIG. 2A) and 30° (FIG. 2B).

Each of the thigh support members 20 is defined by overlapping outer and inner longitudinal sections $20_a$ and $20_b$ which are interconnected in a unique manner that provides for the rapid and easy length adjustment of each of the thigh support members 20 to accommodate legs of varying lengths. In a similar fashion, each of the calf support members 22 is defined by a pair of overlapping outer and inner longitudinal sections $22_a$ and $22_b$ which are adjustably interlocked in the same manner as the longitudinal sections which define each of the thigh support members.

This adjustable interlock between the overlapped longitudinal sections of each of the support members 20, 22 is illustrated in a greater detail in FIG. 3 which depicts in exploded fashion overlapping end portions of the sections $20_a$ and $20_b$ of one of the thigh support members 20. The adjustable interlocking structure provided on the sections $20_a$ and $20_b$ is identical to that provided on the overlapping sections $22_a$ and $22_b$ of each of the calf support members 22.

The outer longitudinal section $20_a$ in FIG. 3 has formed therethrough a longitudinally spaced series of laterally extending circular openings 26. The openings 26 are equally spaced along the section $20_a$, and each adjacent pair of such openings is adapted to laterally receive a longitudinally spaced pair of cylindrical, lateral projections 28 secured to the inner support member section $20_b$ adjacent its outer end. The overall length of the illustrated thigh support member 20 may thus be rapidly and very easily adjusted simply by laterally inserting the projections 28 in different adjacent pairs of the openings 26 to vary the longitudinal overlap between the sections $20_a$ and $20_b$.

With the projections 28 received in an appropriate pair of the openings 26, there is formed a very secure longitudinal and pivotal shear lock between the associated sections $20_a$ and $20_b$ which securely maintains the adjusted length of the thigh support member 20 and prevents relative pivotal motion between the sections $20_a$, $20_b$ along the side of the leg.

To retain the projections 28 in their associated locking openings 26, and thereby prevent lateral separation of the sections $20_a$ and $20_b$, a retaining member in the form of a generally U-shaped clip 32 is provided, the clip having a base wall 34 and a pair of transversely projecting side walls 36. Clip 32 has a support arm portion 38 which is pivotally secured at its outer end to the underside of the section $20_b$ by means of a screw 40 extending downwardly through section $20_b$. Screw 40 is positioned longitudinally inwardly of the projections 28 and is spaced from the nearest projection a distance equal to the longitudinal space between the two projections.

As may be seen by comparing FIGS. 1 and 3, the retaining clip 32 may be pivoted relative to the section $20_b$ (as indicated by the double ended arrow 42 in FIG. 3) between a first position (FIG. 3) in which the clip is swung outwardly to one side of the section $20_b$, and a second position (FIG. 1) in which the clip is swung into frictional engagement with the sections $20_a$ and $20_b$, with the clip side walls 36 respectively engaging upper and lower side surfaces of the overlapping portions of the interlocked sections $20_a$ and $20_b$, over the projections 28, to prevent the lateral separation of the interlocked sections. The inner end of the support member section $20_a$ is provided with a generally semicircular notch 44 which, with the thigh support member 20 adjusted to its longest length (as in FIGS. 2A and 2B), receives the upwardly projecting head of the screw 40. When the member 20 is adjusted to a shorter length (as in FIG. 1), the projecting head of the screw 40 is received in one of the openings 26 to provide a further interlock stability between the sections $20_a$ and $20_b$.

It can be seen that this interlocking structure permits the lengths of the thigh support members 20 to be very rapidly and securely adjusted. All that is necessary to change the overall length of either of the thigh support members is to pivot the retaining clip 32 outwardly, laterally separate the interlocked sections $20_a$ and $20_b$, insert the projections 28 into a different adjacent pair of the openings 26, and then pivot the retaining clip 32 back into locking engagement with the interlocked sections $20_a$ and $20_b$.

As previously mentioned, each of the calf support members 22 is provided with adjustably interlocking structure identical to that just described in conjunction with the thigh support members 20. Specifically, each of the calf support member sections $22_b$ is provided with the lateral projections 28, each of the outer support member sections $22_a$ has formed therethrough the longitudinally spaced series of openings 26, and a clip member 32 is pivotally secured to each of the sections $22_b$ as previously described in conjunction with the thigh support members 20.

The thigh and calf support members 20, 22 are operatively secured to the leg 18 by means of four connecting straps 46, 48, 50 and 52, each of which is secured to the brace 10 and adapted to transversely extend at least partially around the leg 18 and be tightened to hold the support members 20, 22 in place along the leg. In a conventional manner, foam padding elements 54 (illustrated in phantom in FIG. 1 but omitted in FIGS. 2A and 2B) are secured to the brace and wrapped around the leg beneath each of these straps to add to the wearing comfort of the brace. Padding elements 54 are conveniently held in place by hook fabric sections $55_a$ secured to contoured cradle elements 55 connected to the support members 20, 22 as indicated in FIGS. 1, 2A and 2B.

As best illustrated in FIGS. 2A and 2B, strap 46 is positioned adjacent the outer ends 56 of the thigh support members 20, strap 48 is positioned centrally along the thigh support members 20, strap 50 is positioned centrally along the calf support members 22, and strap 52 is positioned adjacent the outer ends 58 of the calf support members 22. Straps 48 and 50 are of conventional construction and operation, and are respectively adapted to be looped around longitudinally central anterior areas of the thigh and calf portions 14, 16 of the leg 12 and be suitably buckled and tightened against these anterior thigh and calf portions to hold the support members 20, 22 in place along the leg.

Figure 4:
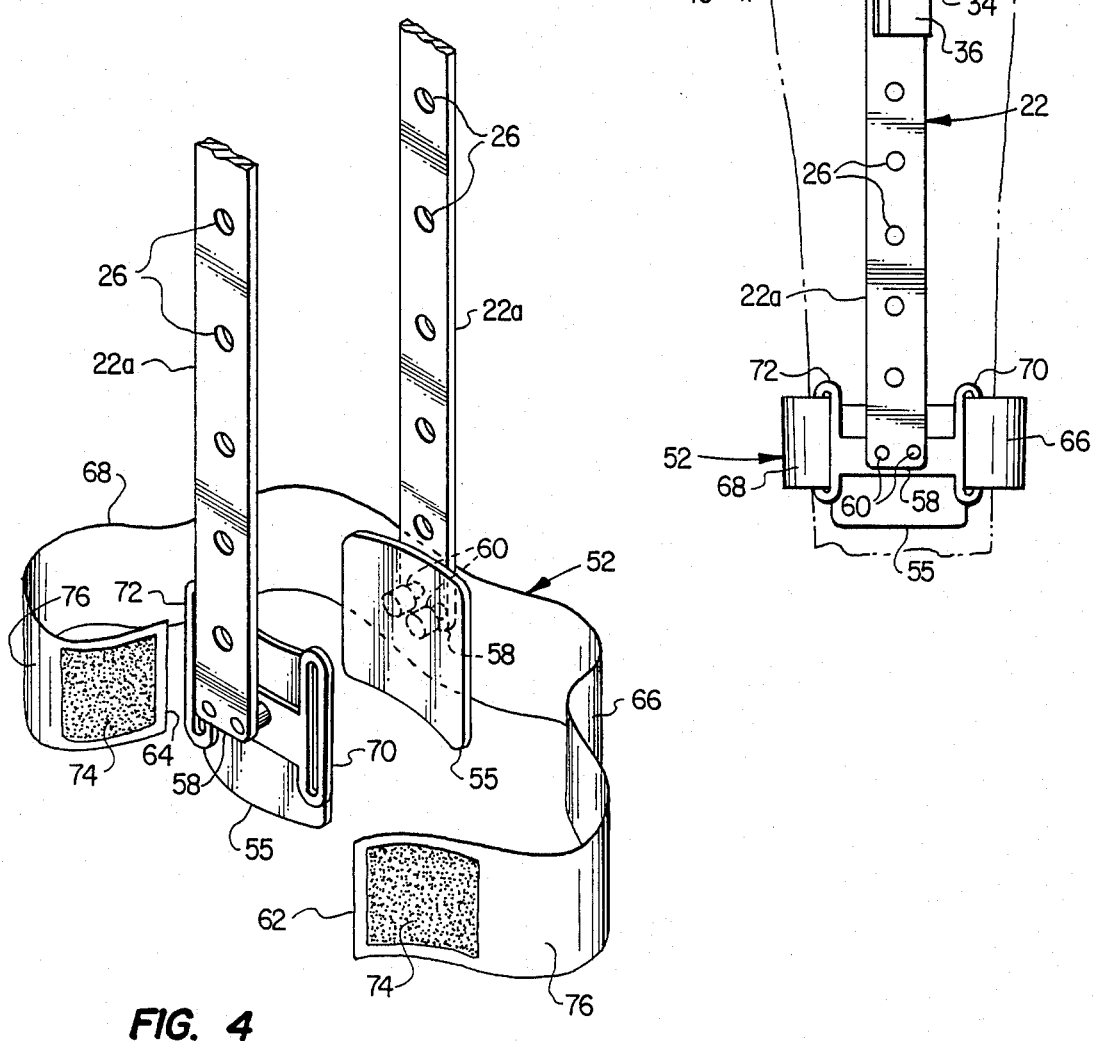
FIG. 4 is a perspective detail view of outer end portions of the two calf support members of the brace and illustrates a single connecting strap secured thereto and having independently adjustable anterior and posterior portions.

However, the straps 46 and 52 are uniquely operative to significantly facilitate and maintain tee initial anterior posterior alignment of the thigh and calf support members 20 and 22 relative to the leg 12. The unique operation of the straps 46 and 52, which are of identical construction and operation, is illustrated in FIG. 4 (see FIG. 1 also) which perspectively depicts outer end portions of the calf support member sections $22_a$ to which the strap 52 is connected. A central longitudinal portion of the strap 52 is anchored to one of the support member sections $22_a$, adjacent its outer end 58, and to one of the cradles 55, by means of rivets 60 or other suitable anchoring members. Outer end portions 62 and 64 of the free strap sections 66 and 68 of the strap 52 are slidably looped through a pair of slotted connector members 70 and 72 secured to the support cradle 55 of the other support member sections $22_a$ adjacent its outer end 58, and then are secured to the strap sections 66 and 68 (as can be best seen in FIG. 1) by means of cooperating hook and pile surfaces 74 and 76 suitably affixed to the strap end portions 62, 64 and their associated strap sections 66 and 68. It can be seen that the strap sections 66 and 68 thus respectively define independently adjustable anterior and posterior sections of the strap 52 which may be selectively and independently tightened or loosened to alter the anterior-posterior orientation of the support member sections $22_a$ on the calf portion 16 of the leg 18.

More specifically, in initially positioning the brace 10 of the leg 12, the articulated side portions of the brace are positioned on the opposite lateral sides of the leg with the locking hinge mechanisms 24 (which have been previously set to their desired pivot stop settings as subsequently described) located on opposite sides of the knee 18 and appropriately aligned therewith. One of the free strap sections 66, 68 of the connecting strap 52 may then be looped through its associated slotted connector member and suitably secured to itself and tightened against the calf portion 16 to precisely align the calf support member sections $22_a$ in a desired anterior-posterior relationship therewith.

For example, if the posterior strap section 68 is looped through the connector 72 first and then adjustably secured to itself via its cooperating hook and pile surfaces 74 and 76, it can be seen that the strap section 68 limits the anterior movement of the support member sections $22_a$. With the adjusted strap section 68 firmly engaging the posterior side of the calf portion 16, the anterior strap section 66 may be looped through its connector member 70 and then secured and tightened to itself to prevent posteriorly directed movement of the support member sections $22_a$.

This same anterior-posterior alignment procedure may then be carried out on the thigh support members 20 by adjustably tightening the independently adjustable anterior and posterior sections 66, 68 of the strap 46 which is identical in configuration and operation to the strap 52 just described. If desired, the anterior section 66 of strap 46 may be suitably connected to a flexible plastic cradle member 78, as illustrated, to provide additional support along an upper thigh portion. Finally, the conventional anterior connecting straps 48 and 50 may be extended around their associated anterior thigh and calf portions of the leg and suitably tightened to complete the connection of the brace 10 to the leg 12.

It is important to note that the straps 46 and 52, with their independently adjustable anterior and posterior portions, significantly facilitate the attachment of the brace 10 to the leg 12 and more effectively maintain the thigh and calf support members 20, 22 in precise anterior-posterior alignment therewith. It was heretofore necessary in conventional knee brace apparatus to manually hold the thigh and calf support members against the leg while wrapping a conventional connecting strap entirely around the leg and then securing the strap to itself. This was a somewhat awkward task which often resulted in undesirable misalignment between the brace support members and the leg to which they were connected. Additionally, essentially the same degree of awkwardness and difficulty was typically associated with altering the anterior-posterior alignment of the support members if it became necessary to change such alignment. However, with the straps 46 and 52, this anterior-posterior alignment may be very rapidly and easily changed simply by loosening one of the separate strap sections 66, 68 and tightening the other strap section.

As previously mentioned, the adjustable hinge mechanisms 24 may be set, in a manner subsequently described, to limit the pivotal motion of the interconnected sets of thigh and calf support members 20, 22 to a predetermined angular range extending between a leg flexion limit angle and a leg extension limit angle. For purposes of illustration herein, the hinge mechanisms 24 have been illustrated in FIGS. 2A and FIGS. 2B as being set to maintain a flexion limit angle of 90° (FIG. 2A) and an extension limit angle of 30° (FIG. 2B).

With the hinge mechanisms 24 being set in this manner, and the support members 20, 22 being firmly strapped to the leg 12 as previously described, the support members 20, 22, due to their firm connection to the thigh and calf portions 14 and 16, theoretically would, without further leg-restraining structure, prevent the leg 12 from being flexed or extended past these two limit ranges. However, it has been found in conventional motion restraining knee braces of this general type that this is not the case—particularly with respect to extension of the leg.

Specifically, because of soft tissue "give", many conventional motion restraining knee braces unavoidably permit the leg to be extended at least somewhat past the extension limit setting of the brace hinges. This has required a trial-and-error technique to be utilized in setting the extension limits of the hinges. For example, if it was medically prescribed that the leg, during the healing process of the knee, be restrained against extension past a 30° flexion angle, it was previously necessary to set the extension limit of the hings at a somewhat greater extension limit angle (i.e., a somewhat larger flexion angle) so that when the leg was slightly overextended due to this soft tissue "give", its maximum extension angle was not less than 30°.

Various additional restraining structure has been previously proposed to at least lessen the capability of the leg to be extended past the extension limit of its restraining brace. For example, one conventional solution to this potential leg over-extension problem has been to connect to the brace a posterior restraining strap which may be tightened against the leg directly behind the knee joint. This technique provides a strong restraining force on the leg which markedly reduces its capability to be extended past the extension limit of the brace. However, the positioning of this transversely extending single posterior strap directly along the bend of the knee interferes with the flexure of the leg and can cause considerable patient discomfort during such flexure. Accordingly, the motion restraining benefit of this single posterior strap is for the most part offset by the patient discomfort it causes.

To lessen this undesirable patient discomfort, various conventional motion restraining knee braces have been provided with a pair of posterior restraining straps which are adapted to transversely extend along posterior portions of the leg above and below the knee joint and which may be tightened against the rear surface of the leg. While this proposed solution to the leg overextension problem reduces patient discomfort, it also is considerably less efficient in preventing overextension of the leg. This is due to the fact that the dual transverse strap restraint system used in various conventional braces moves the extension-inhibiting force areas away from the most effective point-namely, directly behind the knee.

Additionally, neither the single transverse posterior strap positioned directly behind the knee, or the two transversely extending posterior straps positioned above and below the knee, in any manner compensate for the progressive extension strength of the human leg as it approaches its fully extended position. Specifically, whether the single lateral strap or the dual lateral strap approach is utilized, each of the straps must be tightened against the leg to be at all effective in inhibiting overextension of the leg. However, as the leg approaches its fully extended position is potential extension force automatically increases as previously mentioned. Accordingly, the closer the leg is moved toward its fully extended position, the more transverse restraining force is required to prevent the leg, via soft tissue "give", from being overextended. This interplay between the leg's angular position and its available extension force is simply not compensated for by conventional restraining strap structures.

This is due to the fact that such restraining straps, when tightened against the leg, can maintain only a given anteriorly directed restraining force against the leg even when it is moved from a flexed position toward a more extended position. However, as the leg is moved toward a more extended position, more restraining force is required—an increase in force which is unavailable in conventional restraining strap structures. If the degree of tightness in the straps is increased to provide greater restraint against leg extension as the leg is moved toward its fully extended position, the straps may easily be made uncomfortably tight against the leg in other positions thereof.

To solve this leg overextension problem, the present invention provides a uniquely constructed and operative restraining strap network 80 (FIGS. 2A, 2B and 5) which is significantly more effective and appreciably more comfortable than previous extension-inhibiting leg strap structures. Strap network 80 includes a pair of restraining straps 82 and 84 which are carried on the support members 20, 22 by means of four slotted connector members 86, 88, 90 and 92 which are secured to the support members 20, 22 and positioned posteriorily thereof. Connectors 86, 88 are respectively secured to the support member sections $20_b$, $22_b$ of one of the pivotally interconnected sets of thigh and calf support members on opposite sides of its hinge mechanism 24, while the connectors 90, 92 are respectively secured to the support member sections $20_b$ and $22_b$ of the other set of pivotally connected thigh and calf support members on opposite sides of its hinge mechanism 24.

Figure 5:
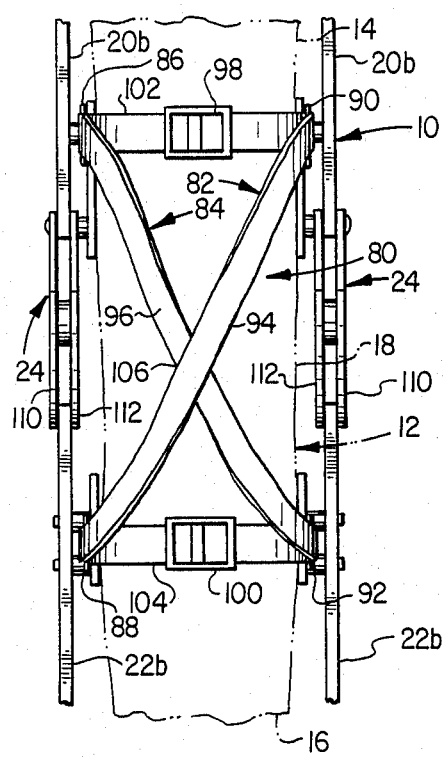
FIG. 5 is a posterior elevational view of a longitudinally central portion of the brace, taken along elevation line 5—5 of FIG. 2B, and illustrates a unique criss-crossed restraining strap structure which functions to inhibit extension of the leg past the extension limit angle setting of the brace.

As best illustrated in FIG. 5, the strap 82 is looped through the connectors 88 and 90 so that a central portion 94 of the strap 82 extends diagonally between the connectors 88 and 90. In a similar manner, the strap 84 is looped through the connectors 86 and 92 so that a central portion 96 of the strap 84 extends diagonally between the connectors 86 and 92. The adjacent free ends of the straps 82, 84 are connected to one another by adjustable buckle means 98 and 100 to define opposite end portions 102, 104 of the strap network 80, the network having a central portion defined by the crisscrossed central strap portions 94, 96.

It can be seen that the generally hourglass-shaped restraining strap network 80 is carried by the support members 20, 22 entirely posteriorily of the leg 12 and is positioned along a longitudinal posterior portion of the leg extending from longitudinally above the knee to longitudinally below the knee. The end portions 102, 104 of the network 80 extend transversely around posterior halves of the leg 12, and the central strap portions 94, 96 cross at a point 106 positioned directly behind the knee 18.

By comparing FIGS. 2A and 2A it can also be seen that as the leg 12 is moved toward its extension limit position, the connector pairs 86, 90 and 88, 92 are moved further apart as the angle between the thigh support members 20 and the calf support members 22 is increased. This increase in the distance between such connector member pairs increasingly tightens the strap network 80 against the back of the leg as the leg approaches its extension limit position.

Importantly, since the restraining straps 82, 84 are slidably looped through the connector members 86, 88, 90 and 92 as previously described, this tightening of the strap network 80 equally tightens each of the separate segments 94, 96, 102 and 104 of the network 80 against the leg to apply thereagainst a progressively increasing, anteriorily directed force which inhibits extension of the leg beyond the extension limit angle setting of the hinge mechanisms 24. Stated in a different manner, the uniquely configured strap network 80, together with its slidable looped connection to the brace support members, maintains each portion of the strap network 80 in essentially equal tension as the network is gradually tightened against the back of the leg. This equalized tension is maximized at the point in which the brace reaches its extension limit setting. Similarly, when the leg is again flexed toward its flexion limit angle, each segment of the restraining strap network is maintained in equal tension with all the other segments and is progressively loosened against the back of the leg until the leg reaches its flexion limit angle.

Thus, the extension limiting restraining force of the strap network 80 closely tracks the available extension strength of the leg 12, the restraining force being maximized at the extension limit of the leg and being minimized at the flexion limit thereof. While both the transverse end portions 102, 104 and the criss-crossed central portions 94, 96 of the network 80 are progressively tightened against the leg across a posterior longitudinal portion thereof extending above and below the knee, the central portions cannot be pinched between adjacent thigh and calf portions of the leg as the leg is being flexed. This, of course, eliminates the previous discomfort present in restraining structures which use a single posterior strap extending transversely around the leg directly behind the knee.

The end sections 102, 104 of the network also provide a considerable improvement over conventional dual transverse restraining strap structure providing only a single level of tightness against the leg. Such end portions, as previously described, are automatically loosened or tightened as the leg is flexed or extended so that the extension restraining force of the network exerts a maximum extension-inhibiting force when such maximum force is needed, and comfortably lessens the force as the leg is pivoted away from its crucial extension limit. Either of the buckle means 98, 100 on the network end portions 102, 104 may be loosened or tightened to adjustably vary the tension of the network 80 with the leg in a fixed pivotal position.

Referring now to FIGS. 6-10, each of the adjustable locking hinge mechanisms 24, which pivotally interconnects one of the thigh support member inner sections $20_b$ to its associated calf support member inner sections $22_b$, includes a pair of outer and inner metal base plates 110 and 112 which are identically configured. Each of the base plates 110, 112 has a generally circular body portion 114 from which a generally rectangular connecting tab portion 116 tangentially extends. Formed through the body portions 114 are an aligned pair of arcuate extension slots 118 which are positioned adjacent the peripheries of the body portions. Circumferentially spaced from the aligned slots 118 are an aligned pair of arcuate flexion slots 120 which are also positioned adjacent the peripheries of the circular body portions 114. Slots 118 have circumferentially unobstructed radially outer portions 122, while the slots 120 have similarly unobstructed radially outer portions 124.

The radially inner side of each slot 118 is provided with seven radially inwardly extending notches 126, each of such notches being circumferentially spaced from its immediately adjacent notch or notches by an angle of 15°. As will be subsequently described, the uppermost notches 126 in the plates 110, 112 (as viewed in FIG. 10) correspond to an extension limit angle of 0° (at which the leg is fully straightened), with each clockwise successive notch 126 adding 15° to such extension limit angle so that the lowermost notches 126 in the plates 110, 112 in FIG. 10 correspond to an extension limit angle of 90°.

In a similar manner, each of the radially inner sides of the aligned flexion slots 120 has formed therein ten radially inwardly extending notches 128 circumferentially spaced apart from one another by an angle of 15°. The circumferentially uppermost notches 128 in the plates 110, 112 in FIG. 10 correspond in a manner subsequently described to a flexion angle of 135°, with each counterclockwise successive notch 128 reducing such flexion limit angle by 15° so that the notches 128 at the right ends of the slots 120 correspond to a flexion limit angle of 0°.

An inner end portion of one of the thigh support member sections 20$_b$ is sandwiched between and anchored to the connecting tabs 116 by means of three rivets 130 which are extended through aligned openings 132 (FIG. 10) formed through the tabs 116 and the support member section 20$_b$. An inner end portion 134 of one of the calf support member sections 22$_b$ is also sandwiched between the body portions 114 of the base plates 110, 112. End portion 134 has formed therethrough a circular opening 136 which is aligned with somewhat smaller central circular openings 138 formed through the base plate body portions 114. The inner end portion 134 of the support member section 22$_b$ is also provided along its right edge (as viewed in FIG. 10) with a lateral projection 140 having formed thereon a concave, arcuately shaped extension stop surface 142. Formed along the opposite edge of the support member section 22$_b$ is a concave, arcuately shaped flexion stop surface 144.

The illustrated hinge mechanism 24 is also provided with an adjustment member in the form of a circular dial element 146 having a base wall 148 from which an annular peripheral flange 150 axially projects. Base wall 148 has a cylindrical, central depression 152 formed therein which projects axially in the same direction as the flange 150. Depression 152 has an inner end wall 154 having a central opening 156 formed therethrough. Also projecting in the same direction from the base wall 148 are a pair of cylindrical posts 158. Formed through the base wall 148 adjacent the radially inner surface 160 of flange 150 are a circumferentially spaced series of circular observation holes 162, each of the holes 162 being spaced apart by 15° from its immediately adjacent hole or holes.

Projecting radially outwardly from the dial flange 150 are a pair of generally V-shaped tabs 164 and 165 which define therebetween a generally V-shaped exterior notch 166. Circumferentially aligned with the notch 166 is a curved depression 168 which extends radially outwardly into the inner surface 160 of the dial flange 150. The depression 168 communicates with a slot 170 which extends radially inwardly along the dial member base wall 148 from its juncture with the inner flange surface 160. A generally V-shaped spring member 172 is carried within the body of the dial 146 and has a pair of leg portions 174 which are wrapped around the posts 158 (see FIGS. 9A and 9B) with the apex portion 176 of spring 172 being aligned with the dial flange internal depression 168.

The dial 146 is rotatably mounted, flange side down, on the outer side surface of the base plate 110 by means of a rivet 178 that extends sequentially through a washer 180, the central dial opening 156, the central opening 138 in the base plate 110, an annular bushing 182 rotatably received in the support member opening 136, the central opening 138 in the base plate 112, and a central opening 184 in a plastic support disc 186 positioned below the base plate 112 as viewed in FIG. 10. On its outer side surface 188, the disc 186 has secured thereto a strip of hook fabric 190 (FIG. 1) which is attachable to a foam padding disc (not illustrated) that is positionable against one side of the knee. The head 192 of the rivet 178 is recessed within the depression 152 formed in the base wall 148 of the dial 146. A thin plastic trim disc 194 (see, e.g., FIG. 6) may be suitably adhered to the dial base wall 148 to cover the open end of the cylindrical recess 152.

Figure 9A:
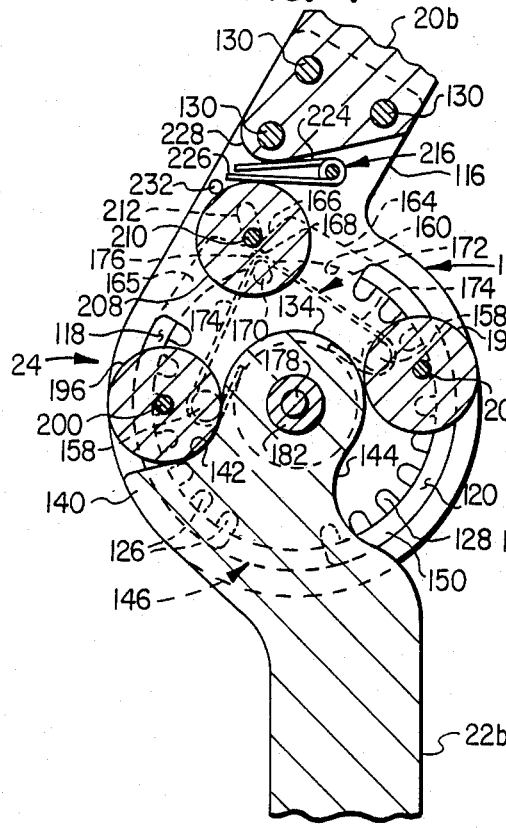
FIGS. 9A and 9B are cross-sectional views through the hinge assembly, taken along line 9—9 of FIG. 7, and respectively illustrate the interconnected support members at their extension and flexion angle limits.
Figure 9B:
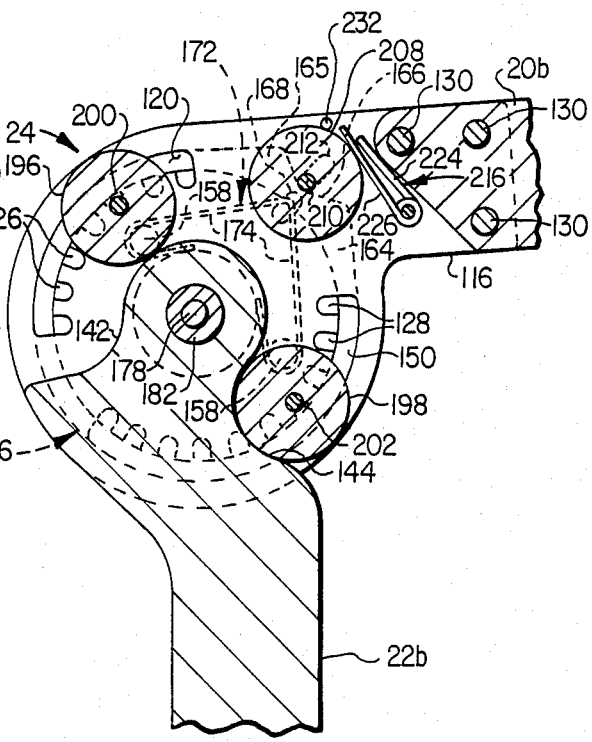

The rivet 178 which interconnects the hinge elements 146, 110, 112 and 186 also mounts the support member section 22$_b$ to the hinge for pivotal motion in clockwise and counterclockwise directions relative to the support member section 20$_b$. Referring now to FIGS. 9A, 9B and 10, to limit this relative pivotal motion to an angular range extending between the extension and flexion limit angles of the brace 10, a pair of pivot stop members in the form of an extension limit disc 196 and a flexion limit disc 198 are utilized. Discs 196 and 198 are sandwiched between the base plates 110 and 112, and are respectively provided with central locking pin portions 200 and 202 which project axially outwardly from the opposite side surfaces of their associated limit disc.

After the hinge mechanism 24 has been adjusted in a manner subsequently described, the opposite ends of the locking pin 200 are received in circumferentially aligned pairs of the extension slot notches 126 in the base plates 110 and 112, and opposite ends of the locking pin 202 are received in circumferentially aligned flexion slot notches 128 in the base plates 110, 112. Upper end portions of the locking pins 200, 202 (as viewed in FIG. 10) project upwardly from the upper side surface of base plate 110 and are engaged by the radially inner surface 160 of the dial flange 150 to thereby captively retain these locking pins in their respective slot notch pairs. Captively retained in the slot notches in this manner, the pins 200, 202 are prevented from moving circumferentially around their associated slots 118, 120 to thereby lock the discs 196, 198 in their relative circumferential orientation with respect to the base plates 110, 112 as representatively illustrated in FIG. 9A.

Accordingly, the locked disc 196 functions to limit the angular extension between the support member sections 20$_b$ and 22$_b$ by engaging the stop surface 142 on the support member section 22$_b$ (FIG. 9A), while the disc 198 functions to limit the flexion motion between the support member sections 20$_b$ and 22$_b$ when the stop surface 144 of support member section 22$_b$ is brought into engagement with the locked disc 198 (FIG. 9B). It can readily be seen by comparing FIGS. 9A and 9B that the locked discs 196, 198 thus function to limit the relative pivotal motion of the support member sections 20$_b$, 22$_b$ to a predetermined angular range extending from a representative extension limit angle of 30° (FIG. 9A) and a representative flexion limit angle of 90° (FIG. 9B).

Figure 6:
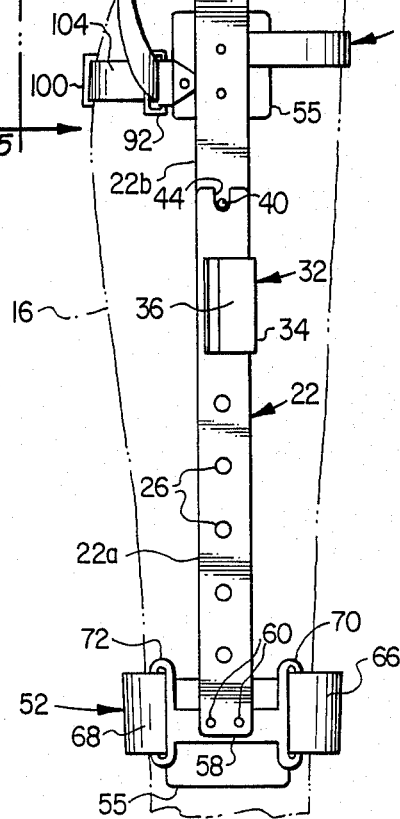
FIG. 6 is a perspective view of one of the two adjustable hinge mechanisms used to pivotally interconnect the two thigh and calf support member sets on opposite lateral sides of the leg, portions of the interconnected support members being illustrated in phantom.
Figure 7:
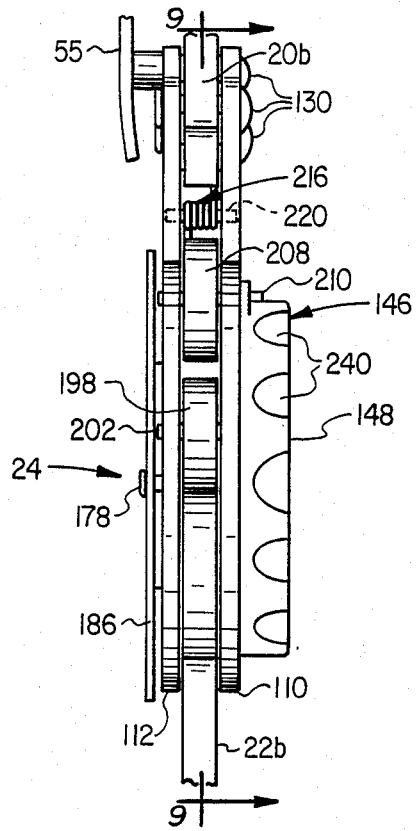
FIG. 7 is a left side elevational view of the hinge mechanism.
Figure 8:
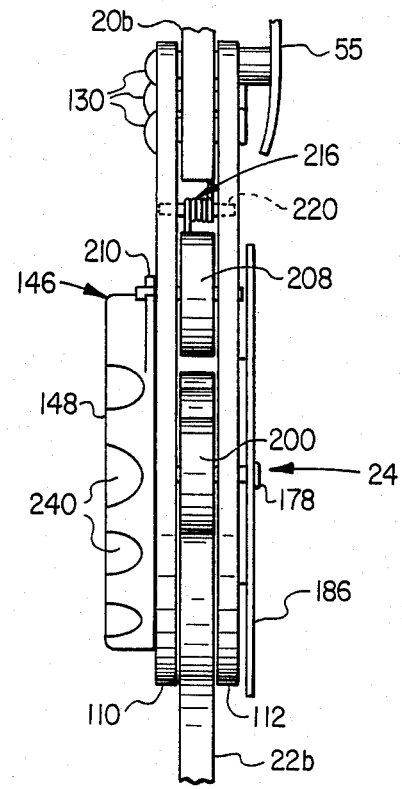
FIG. 8 is a right side elevational view of the hinge mechanism.

The relative angular orientations of the locking pins 200, 202 in their associated pairs of slots 118 and 120, and thus the relative positions of the pivot stop discs 196 and 198, are visually ascertainable simply by looking into the observation holes 162 formed in the base wall 148 of the hinge dial 146. As illustrated in FIG. 6, the pins 200, 202 are readily visible through a pair of these observations holes 162 which are aligned with the pins, regardless of their relative orientation, when the dial 146 is in its locked position as subsequently described. The visually determinable location of the pins 200, 202 may be easily correlated with extension and flexion angle indicia markings 204 and 206 suitably imprinted on the outer side surface of the base plate 110 around the periphery of its circular body portion. By observing which of these angle markings the particular locking pin is aligned with, both the flexion and extension limit settings of the hinge may be rapidly ascertained simply by looking at the dial.

As previously mentioned, with the illustrated hinge mechanism 24 in a predetermined, adjusted position, the locking pins 200 and 202 are captively retained at their opposite ends within circumferentially aligned pairs of slot notches 126 and 128 on the laterally spaced base plates 110 and 112 by the inner surface 160 of the dial flange 150 to thereby circumferentially lock the extension and flexion pivot stop discs 196 and 198 relative to the base plates. After the pins 200, 202 have been positioned in selected slot notch pairs, in a manner subsequently described, the dial 146 is rotated to its lockable position illustrated in FIG. 6, with the triangular dial tabs 164 and 165 facing generally upwardly as viewed in FIG. 6. According to another unique aspect of the present invention, the dial 146 may be rapidly and securely locked in this position by the physician or physical therapist who initially adjusts the hinge mechanism to prevent (or at least significantly hinder) subsequent rotation of the dial 146, and undesirable readjustment of the pin settings, by the patient upon whose leg the brace is operatively secured.

Figure 10:
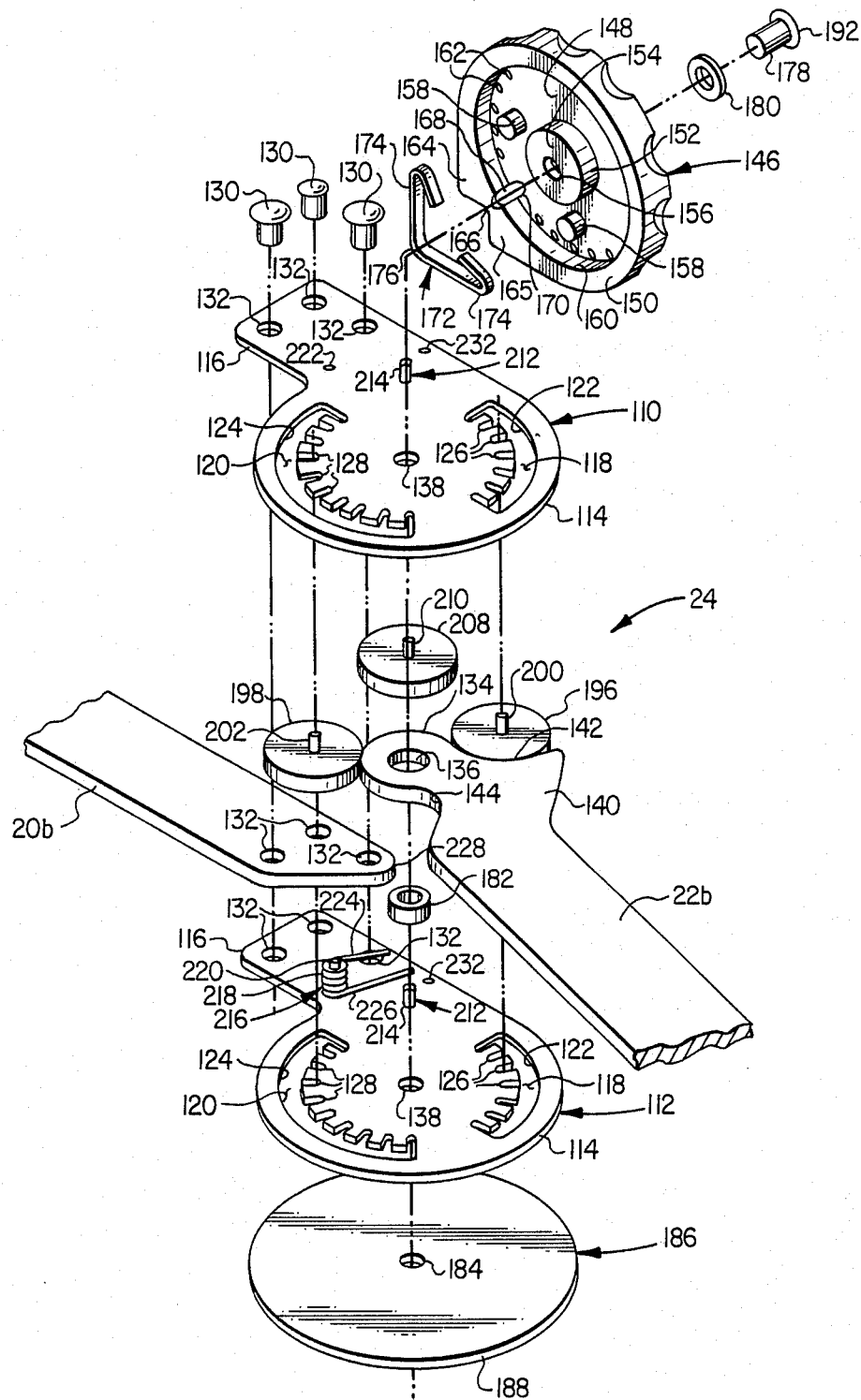
FIG. 10 is an exploded perspective view of the hinge assembly.

Referring now to FIGS. 6 and 10, this tamper-proof locking of the dial 146 is made possible by the provision of a dial locking disc 208 (FIG. 10) which is essentially identical in size and configuration to the pivot stop discs 196 and 198. The dial locking disc 208 is provided with a central, axially projecting locking pin 210 which is slidably received at its opposite ends in a pair of generally radially extending slots 212 formed through the base plates 110, 112 adjacent the junctures of their circular body portions 114 and connecting tabs 116. Like the discs 196 and 198, the dial locking disc 208 is sandwiched between the base plates 110 and 112.

The pin 210 is biased toward the radially inner ends 214 of the slots 212 (FIG. 10) by means of a small spring element 216 carried between the plates 110 and 112. Spring element 216 has a coiled central portion 218 which receives a small pin 220 carried at its opposite ends in a pair of small circular openings 222 (only one of which is visible in FIG. 10) formed through the connecting tabs 116 of the base plates 110, 112. Extending transversely in the same direction from opposite ends of the coiled central spring portion 218 are a pair of spring arms 224, 226 which, as best illustrated in FIG. 9A and 9B, respectively bear against the inner end 228 of the support member section 20$_b$ and the dial locking disc 208. The force of spring arm 226 on the disc 208 resiliently urges the locking pin 210 inwardly along the slots 212 and biases the pin 210 toward its illustrated position at the inner ends of such slots 212.

When the dial 146 is rotated toward its lockable position illustrated in FIG. 6, the outer side surface of one of the triangular dial tabs 164, 165 engages a portion of the pin 210 which projects outwardly through the slot 212 in the outer base plate 110 and, as the dial is rotated further toward its lockable position, urges the pin 210 outwardly along its retaining slots 212 against the biasing force of the spring element 216. As the apex of the triangular dial tab passes beneath the outwardly projecting portion of the pin 210, the spring 216 forces such outwardly projecting pin portion inwardly into the exterior dial notch 168 so that with the dial in the position illustrated in FIG. 6 and the outwardly projecting portion of pin 210 rests in the bottom of the dial notch 168.

After the pivot disc pins 200, 202 have been locked in appropriate pairs of the slot notches 126 and 128, and the dial 146 has been moved to its lockable position, the dial 146 may be locked to prevent patient tampering with the hinge setting. This locking of the dial is accomplished by threading a plastic locking tie member 230 (FIG. 6) through a pair of small circular openings 232 formed through the base plates 110, 112 adjacent the pin slots 212, and then locking the tie to itself by inserting an end portion 234 of the tie through a ratcheted buckle portion 236 thereof. Once the end portion 234 is inserted through the buckle 236, it cannot be pulled outwardly therethrough, and the tie 230 must be cut to remove it from the openings 232.

The portion of the plastic locking tie 230 which extends through the openings 232 is positioned radially outwardly of and closely adjacent the periphery of the dial locking disc 208. Accordingly, such portion of the locking tie prevents appreciable radially outward movement of the dial locking disc 208 parallel to the slots 212. In turn, this prevents the locking pin 210 from moving outwardly along its retaining slots 212. Held in the position illustrated in FIGS. 6, 9A and 9B by the locking tie 230, the outwardly projecting portion of the pin 210 thus prevents rotation of the dial 146 in either direction. For example, if an attempt is made to turn the dial in either direction, the interengagement between the now fixed outwardly projecting portion of the pin 210 and one of the inner side surfaces of the triangular dial tabs 164, 165 prevent rotation of the dial.

The unique cooperation between the dial 146 and the pivot stop disc locking pins 200, 202 which is utilized to circumferentially reposition either or both of the pivot stop discs 196, 198 will now be described with reference to FIGS. 9A, 11–13 and 11A–13A. For purposes of illustration, it will be assumed that it is desired to change the extension limit angle of the hinge mechanism 24 from 30° (as representatively illustrated in FIG.

9A) to 45°. In order to effect this change in the extension limit angle setting of the hinge, it is necessary to move the locking pin 200 from the pair of slot notches 126 corresponding to the 30° extension limit setting to the next adjacent pair of slot notches 126 corresponding to an extension limit angle setting of 45°. More specifically, as viewed in FIG. 9A, the locking pin 200 needs to be moved down one notch along the slots 118.

Figure 11:
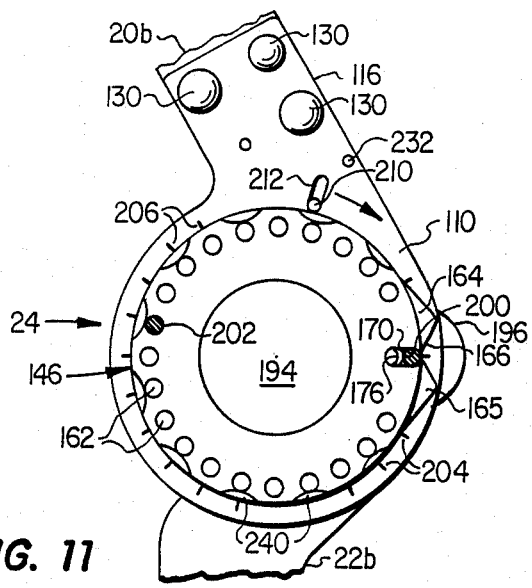
FIGS. 11-13 are front elevational views of the hinge mechanism sequentially illustrating certain adjustment steps used to selectively alter the position of one of its internal pivot stop members.
Figure 11A:
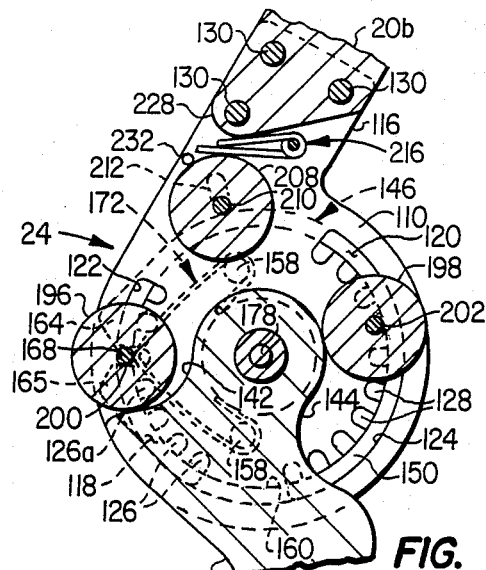

To accomplish this relocation of the pin 202, the locking tie 230 is first cut and removed from its openings 232 to permit rotation of the dial 146. Dial 146, as viewed in FIGS. 6 and 11-13, is then rotated in a clockwise direction away from its previously locked position until the exterior dial notch 166 is brought into alignment with the locking pin 200 of the extension pivot stop disc 196 (FIGS. 11 and 11A). Slightly before the dial 146 is brought to this position, the apex 176 of the spring 172 engages the locking pin 200 and resilient urges it radially outwardly from its initial pair of slot notches 126 and into the depression 168 formed in the inner surface of the dial flange 150. This radially outward movement of the locking pin 200 carries it into the circumferentially unobstructed radially outer portions 122 of the extension slots 118. Such radially outward movement of the pin 200 also causes the pivot stop disc 196 to pop outwardly beyond the peripheries of the base plates 110, 112 as illustrated in FIGS. 11 and 11A. In this popped-out position, the disc 196 is both visible and manually accessible by the physician or technician performing the hinge adjustment. The locking pin 200 in the position thereof illustrated in FIGS. 11 and 11A, is captively retained in the dial surface depression 168 by the apex 176 of the spring element 172. Accordingly, the captively retained pin 200 is now held by the dial 146 for rotational movement therewith so that the pin 200 may be moved around the unobstructed radial portion 122 of the extension slot 118.

Figure 12:
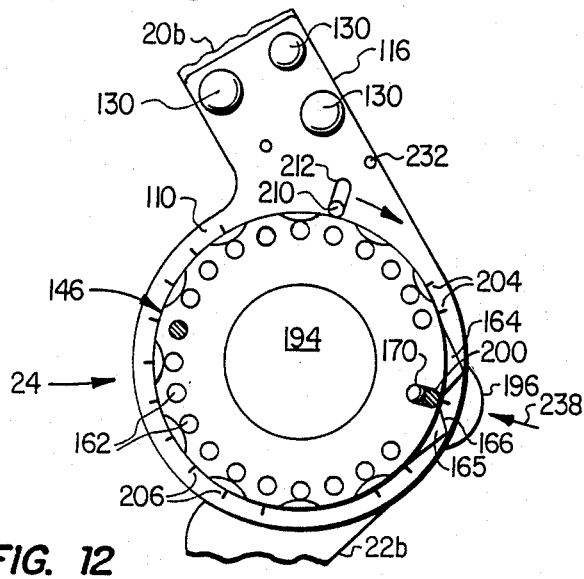
Figure 12A:
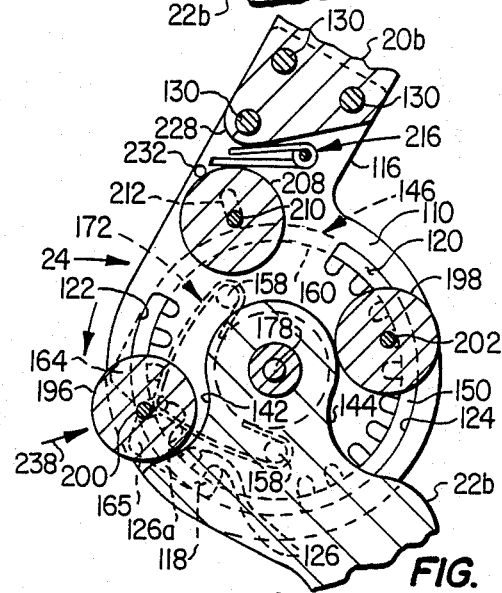
Figure 13:
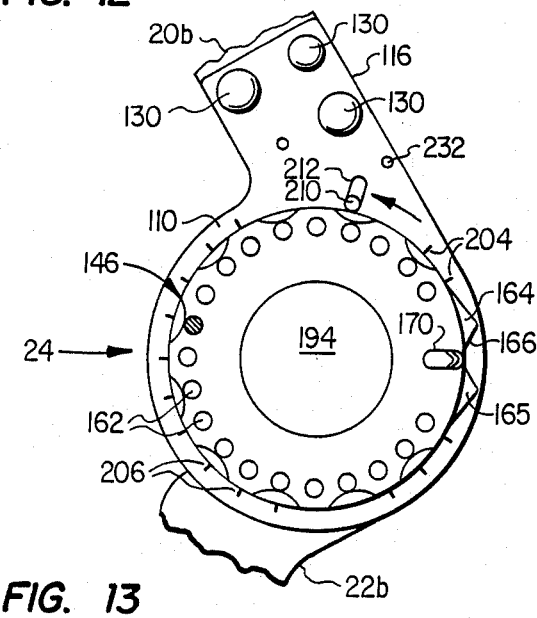
Figure 13A:
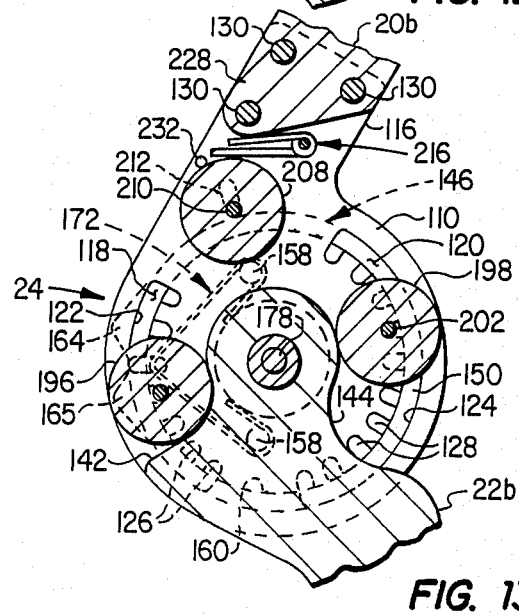

Next, the dial 146 is rotated 15° in a clockwise direction (as viewed in FIG. 12) to move the pin 200 along its slots 118 to bring it into circumferential alignment with a new pair of notches 126$_a$ (FIG. 12A) which correspond to an extension limit angle of 45°. This clockwise circumferential movement of the pin 200 in FIG. 12 appears as a counterclockwise movement of such pin in FIG. 12A. The repositioned pivot stop disc 196 is then manually pushed radially inwardly between the base plates 110, 112, as indicated by the arrows 238 in FIGS. 12 and 12A, to force the locking pin 200, against the biasing force of the spring element 172, into the aligned pair of slot notches 126$_a$.

The disc 196 is then manually held in this position while the dial 146 is rotated in a counterclockwise direction (FIG. 13) toward its lockable position (FIG. 6) to thereby disengage the spring apex 176 from the pin 200 and move the inner surface 160 of the dial flange 150 into engagement with the pin 200 to thus captively retain the pin in its new pair of slot notches 126$_a$. The dial 146 may then be further rotated in a counterclockwise direction until it reaches its lockable position in which the pin 210 is received in the exterior dial notch 166. A new locking tie may then be threaded through the base plate openings 232 to again rotationally lock the dial as previously described. The hinge mechanism 24 in its readjusted position has a flexion limit angle of 90° and an extension limit angle of 45°.

If desired, of course, the circumferential position of the flexion locking pin 202 may also be altered, before or after the adjustment of the extension locking pin 200 in a manner similar to that just described, before a new locking tie is utilized to rotationally lock the dial.

From the foregoing it can be seen that each of the hinge mechanisms 24 of the present invention may be rapidly and very easily adjusted to alter either or both of the extension and flexion angle limits thereof. The locking pins 200, 202 provide very secure shear locks between the discs 196, 198 and the base plates 110, 112 to firmly prevent the pivotally interconnected thigh and calf support members 20, 22 from moving beyond the angular stop settings of their associated hinge. While the hinge mechanisms 24 have several movable parts, such parts are captively retained between the base plate portions of the hinge so that they cannot become dislodged or lost during or after adjustment of the hinge. The unique operation of the dial locking disc 208 permits the hinge mechanisms to be easily rendered essentially tamper proof, but may be easily prepared for professional adjustment simply by cutting and removing the plastic locking tie. The actual setting of each of the hinge mechanisms is readily visible simply by viewing the positions of the locking pins 200, 202 through the observation holes 162 formed in the dial. To facilitate the manual rotation of the dial 146, a circumferentially spaced series of small finger depressions 240 are formed around the periphery thereof.

Coupled with the previously described rapid length adjustment capabilities of the support members 20 and 22, the independent anterior and posterior adjustment features of the connecting straps 46 and 52, and the novel leg extension restraining strap network 80, these improved hinge mechanisms 24 afford the brace 10 with an advantageous variety of significant structural and operational improvements over previously utilized motion restraining knee braces of this general type.

The foregoing detailed description is to be clearly understood as given by way of illustration and example, the spirit and scope of the present invention being limited solely by the appended claims.

What is claimed is:

1. Motion restraining knee brace apparatus comprising:
   first and second elongated thigh support members respectively positionable to extend along first and second lateral sides of a thigh portion of a human leg;
   first and second elongated calf support members respectively positionable to extend along first and second lateral sides of a calf portion of the leg, each of said thigh and calf support members having:
   a first longitudinal section having an opening means formed therein,
   a second longitudinal section having protruberance means formed thereon for releasable insertion, in a first lateral direction, into a selected portion of said opening means to selectively vary the length of the support member, and to longitudinally and pivotably lock said first and second longitudinal sections thereof, and
   retaining means carried by one of said first and second longitudinal sections for movement relative thereto between a first position in which said first and second longitudinal sections may be separated in said first lateral direction, and a second position in which said retaining means prevent their separation in said first lateral direction;

connecting means for operatively securing said thigh and calf support members to the leg, said connecting means including:
  first strap means interconnectable between said thigh support members and adapted to generally encircle said thigh portion of the leg, and
  second strap means interconnectable between said calf support members and adapted to generally encircle said calf portion of the leg;
first hinge means, positionable adjacent a knee portion of the leg, for pivotably interconnecting facing end portions of said first thigh support member and said first calf support member;
second hinge means, positionable adjacent said knee portion of the leg, for pivotably interconnecting facing end portions of said second thigh support member and said second calf support member, each of said first and second hinge means being adjustable to selectively limit the relative pivotal movement of its associated support members to a predetermined angular range extending between selectively variable extension and flexion limit angles, each of said first and second hinge means including:
  base means,
  a duality of stop members each carried by said base means for translational movement relative thereto into a selected one of a series of positions thereon,
  adjustment means, carried by said base means for movement relative thereto, and
  cooperating means on said base means, said duality of stop members and said adjustment means for sequentially:
    causing said adjustments means, during a first movement thereof relative to said base means, to engage a selected one of said duality of stop members and move it away from an initial position thereof on said base means,
    permitting the stop member moved by said adjustment means to be manually moved to a second position on said base means, and
    locking the manually moved stop member on said base means in said second position on said base means,
  first attachment means for anchoring an end portion of one of the support members associated with the hinge means to its base means, and
  second attachment means for connecting an end portion of the other of the support members associated with the hinge means to its base means for pivotal motion relative thereto between and into motion-limiting engagement with the first and second stop members carried thereby; and
flexible restraining means, carried by said thigh and calf support members, for inhibiting extension of the leg beyond said extension limit angle, said flexible restraining means being:
  positionable entirely posteriorly of the leg,
  configured to longitudinally span and exert pressure against a posterior longitudinal portion of the leg extending from longitudinally above the knee to longitudinally below the knee, and having opposite end portions positioned and configured to laterally span and exert pressure against opposite ends of said posterior longitudinal portion, in response to extension of said leg,
  operative to be progressively and uniformly loosened along said posterior longitudinal portion by said thigh and calf support members as the leg is flexed toward said flexion limit angle, and
  operative to be progressively and uniformly tightened against said posterior longitudinal portion by said thigh and calf support members as the leg is extended toward said extension limit angle.

2. The motion restraining knee brace apparatus of claim 1 wherein:
  said apparatus further comprises first strap connector means carried by one said thigh support members, and second strap connector means carried by one said calf support members,
  said first strap means include a first connection strap having a central portion anchored to the other of said thigh support members, said first connection strap having a pair of free portions with outer ends which may be passed through said first strap connector means, and first tightening means for adjustably tightening each of said pair of free portions against leg, and
  said second strap means include a second connection strap having a central portion anchored to the other of said calf support members, said second connection strap having a pair of free portions with outer ends which may be passed through said second strap connector means, and second tightening means for adjustably tightening each of said pair of free portions of said second connection strap against the leg.

3. The motion restraining knee brace apparatus of claim 2 wherein:
  said first strap connector means include a first pair of connector members having openings formed therethrough,
  said second strap connector means include a second pair of connector members having openings formed therethrough, and
  said first and second tightening means include cooperating hook and pile surfaces formed on said outer ends and said free portions of said first and second connection straps.

4. The motion restraining knee brace apparatus of claim 1 wherein:
  said apparatus further comprises first and second pairs of connector members respectively secured to said thigh support members and to said calf support members, and
  said flexible restraining means include restraining strap means slidably looped through said first and second pairs of connector members to form a generally hourglass-shaped restraining strap network.

5. The motion restraining knee brace apparatus of claim 4 wherein:
  said restraining strap means include first and second restraining straps and buckle means for adjustably intersecuring adjacent free end portion of said first and second restraining straps.

6. Motion restraining knee brace apparatus comprising:
  first and second elongated thigh support members respectively positionable to extend along first and second lateral sides of a thigh portion of a human leg;

first and second elongated calf support members respectively positionable to extend along first and second lateral sides of a calf portion of the leg, each of said thigh and calf support members having:
  a first longitudinal section having opening means formed therein,
  a second longitudinal section having protruberance means formed thereon for releasable insertion, in a first lateral direction, into selected portion of said opening means to selectively vary the length of the support member, and to longitudinally and pivotably lock said first and second longitudinal sections thereof, and
  retaining means carried by one of said first and second longitudinal sections for movement relative thereto between a first position in which said first and second longitudinal sections may be separated in said first lateral direction, and a second position in which said retaining means prevent their separation in said first lateral direction;
connecting means for operatively securing said thigh and calf support members to the leg, said connecting means including:
  first strap means interconnectable between said thigh support members and adapted to generally encircle said thigh portion of the leg, and
  second strap means interconnectable between said calf support members and adapted to generally encircle said calf portion of the leg,
  said first and second strap means each having anterior and posterior portions whose lengths are independently adjustable to thereby precisely position and hold said thigh and calf support members in desired anterior-posterior orientations along said thigh and calf portions of the leg;
first hinge means, positionable adjacent a knee portion of the leg, for pivotably interconnecting facing end portions of said first thigh support member and said first said support member;
second hinge means, positionable adjacent said knee portion of the leg, for pivotably interconnecting facing end portions of said second thigh support member and said second calf support member, each of said first and second hinge means being adjustable to selectively limit the relative pivotal movement of its associated support members to a predetermined angular range extending between selectively variable extension and flexion limit angles, each of said first and second hinge means including:
  base means,
  a duality of stop members each carried by said base means for translational movement relative thereto into a selected one of a series of positions thereon,
  adjustment means, carried by said base means for movement relative thereto, and
  cooperating means on said base means, said duality of stop members and said adjustment means sequentially:
    causing said adjustment means, during a first movement thereof relative to said base means, to engage a selected one if said duality of stop members and move it away from an initial position thereof on said base means,
    permitting the stop member moved by said adjustment means to be manually moved to a second position on said base means, and
    locking the manually moved stop member on said base means in said second position on said base means,
  first attachment means for anchoring an end portion of one of the support members associated with the hinge means to its base means, and
  second attachment means for connecting an end portion of the other of the support members associated with the hinge means to its base means for pivotal motion relative thereto between and into motion-limiting engagement with the first and second stop members carried thereby; and
flexible restraining means, carried by said thigh and calf support members, for inhibiting extension of the leg beyond said extension limit angle, said flexible restraining means being:
  positioned entirely posteriorly of the leg,
  configured to longitudinally span and exert pressure against a posterior longitudinal portion of the leg extending from longitudinally above the knee to longitudinally below the knee and to laterally span and exert pressure against opposite ends of said posterior longitudinal portion,
  operative to be progressively and uniformly loosened along said posterior longitudinal portion of said thigh and calf support members as the leg is flexed toward said flexion limit angle, and
  operative to be progressively and uniformly tightened against posterior longitudinal portion by said thigh and calf support members as the leg is extended toward said extension limit angle,
said opening means including longitudinally spaced series of openings formed through said first longitudinal section,
said protruberance means including a longitudinally spaced duality of lateral projects carried by said longitudinal section and adapted to be releasably inserted in a selected adjacent pair of said openings, and
said retaining means including a clip member pivotally carried by one of said first and second longitudinal sections and, when in said second position, adapted to engage each of said first and second longitudinal sections along overlapping portions thereof.

7. The motion restraining knee brace apparatus of claim 6 wherein:
said clip member has a generally U-shaped body portion, and a support arm portion extending from said body portion and pivotally connected to said second longitudinal section.

8. The motion restraining knee brace apparatus of claim 7 wherein:
said first longitudinal section has an inner end notch, and
said support portion is pivotally connected to said second longitudinal section by a connecting member having an outwardly projecting head portion adapted to be received in said end notch or any of said openings.

9. Motion restraining knee brace apparatus comprising:
first and second elongated thigh support members respectively positionable to extend along first and second lateral sides of a thigh portion of a human leg;

first and second elongated calf support members respectively positionable to extend along said first and second lateral sides of a calf portion of the leg, each of said thigh and calf support members having:

a first longitudinal section having opening means formed therein, a second longitudinal section having protruberance means formed thereon for releasable insertion, in a first lateral direction, into a selected portion of said opening means to selectively vary the length of the support member, and to longitudinally and pivotally lock said first and second longitudinal sections thereof, and retaining means carried by one of said first and second longitudinal sections for movement relative thereto between a first position in which first and second longitudinal sections may be separated in said first lateral direction, and a second position in which said retaining means prevent their separation in said first lateral direction;

connecting means for operatively securing said thigh and calf support members to the leg, said connecting means including:

first strap means interconnectable between said thigh support members and adapted to generally encircle said thigh portion of the leg, and second strap means interconnectable between said calf support members and adapted to generally encircle said calf portion of the leg, said first and second strap means each having anterior and posterior portions whose lengths are independently adjustable to thereby precisely position and hold said thigh and calf support members in desired anterior-posterior orientations along said thigh and calf portions of the leg;

first hinge means, positionable adjacent a knee portion of the leg, for pivotally interconnecting facing end portions of said first thigh support member and said first calf support member;

second hinge means, positionable adjacent said knee portion of the leg, for pivotally interconnecting facing end portions of said second thigh support member and said second calf support member, each of said first and second hinge means being adjustable to selectively limit the relative pivotal movement of its associated support members to a predetermined angular range extending between selectively variable extension and flexion limit angles, each of said first and second hinge means including:

base means, a duality of stop members each carried by said base means for translational movement relative thereto into a selected one of a series of positions thereon, adjustment means, carried by said base means for movement relative thereto, and cooperating means on said base means, said duality of stop members and said adjustment means for sequentially:

causing said adjustment means, during a first movement thereof relative to said base means, to engage a selected one of said duality of stop members and move it away from an initial position thereof on said base means, permitting the stop member moved by said adjustment means to be manually moved to a second position on said base means, and locking the manually moved stop member on said base means in said second position on said base means, first attachment means for anchoring an end portion of one of the support members associated with the hinge means to its base means, and second attachment means for connecting an end portion of the other of the support members associated with the hinge means to its base means for pivotal motion relative thereto between and into motion-limiting engagement with the first and second stop members carried thereby; and flexible restraining means, carried by said thigh and calf support members, for inhibiting extension of the leg beyond said extension limit angle, said flexible restraining means being:

positionable entirely posteriorly of the leg, configured to longitudinally span and exert pressure against a posterior longitudinal portion of the leg extending from longitudinally above the knee to longitudinally below the knee and to laterally span and exert pressure against opposite ends of said posterior longitudinal portion, operative to be progressively and uniformly loosened along said posterior longitudinal portion by said thigh and calf support members as the leg is flexed toward said flexion limit angle, and operative to be progressively and uniformly tightened against said posterior longitudinal portion by said thigh and calf support members as the leg is extended toward said extension limit angle, said base means including a pair of base plates each having formed thereon an arcuate extension slot having a circumferentially spaced series of notches formed along a side thereof, and an arcuate flexion slot having a circumferentially spaced series of notches formed along a side surface thereof, said duality of stop members comprising an extension pivot stop disc and a flexion pivot stop disc each sandwiched between said base plates, said adjustment means including a dial member carried by one of said base plates for rotation relative thereto, and said cooperating means including a central axial locking pin secured to said extension pivot stop disc and having opposite end portions carried in said extension slots adapted to enter and be circumferentially locked in selected notches thereof, a central axial locking pin secured to said flexion pivot stop disc and having opposite end portions carried in said flexion slots and adapted to enter and be circumferentially locked in selected notches thereof, an annular flange on said dial member having an enternal side surface portion adapted to engage said locking pins and captively retain them in notches of said extension and flexion slots, a depression formed in said internal side surface of said annular flange and adapted to radially receive an outer end of one of said locking pins, and a spring member carried by said dial member, said spring member being adapted to engage and resiliently urge said outer end of one of said locking pins into said depression and resiliently retain it in the depression for rotational movement with said dial member.

10. The motion restraining knee brace apparatus of claim 9 further comprising:
    locking means for selectively locking said dial member against rotation relative to said base plates.

11. The motion restraining knee brace apparatus of claim 10 wherein said locking means include:
    a pair of aligned locking slots formed in said base plates,
    a locking disc sandwiched between said base plates and movable relative thereto, said locking disc having a central axial pin portion carried at opposite ends in said locking slots so that said locking disc may be moved between first and second positions relative to said base plates, said central axial pin portion having an outer end projecting outwardly from the base plate upon which said dial member is mounted,
    an external notch formed in the periphery of said dial member and defined by outwardly projecting side portions of said dial member, said external notch being adapted to receive said projecting outer end of said central axial pin portion,
        said projecting outer end of said central axial pin portion, when received in said external notch with said locking disc held in said first position, cooperating with side portions to prevent rotation of said dial member relative to said base plates,
    spring means for resiliently biasing said locking disc toward said first position and permitting said locking disc to be moved to said second position by engagement of either of said outwardly projecting side portions with said projecting outer end of said central axial pin portion to thereby permit said outwardly projecting side portions to be rotated past said projecting outer end of said central axial pin portion against the biasing force of said spring means, and
    holding means for selectively holding said projecting outer end of said central axial pin portion in said external notch on said dial member.

12. The motion restraining knee brace apparatus of claim 11 wherein:
    said holding means include a pair of aligned openings formed through said base plates and adapted to receive a blocking member which blocks movement of said locking disc from said first position toward said second position.

13. Knee brace apparatus having a leg support portion comprising:
    a duality of elongated leg support members positionable along opposite lateral sides of a longitudinal portion of a human leg, each of said leg support members including separate first and second longitudinal sections;
    connecting means for operatively securing said leg support members to the leg; and
    interconnecting means for releasably interconnecting the first and second longitudinal sections of each of said leg support members in a manner permitting the lengths of said leg support members to be rapidly adjusted, said interconnecting means including:
        opening means in each of said first longitudinal sections,
        projection means formed on each of said second longitudinal sections and being releasably insertable, in a first lateral direction, into a selected portion of the opening means in an associated first longitudinal section to create pivotal and translational shear locks between each associated set of first and second longitudinal sections, and
        retaining clip means pivotally carried by one of first and second longitudinal sections in each set thereof at a fixed location thereon for pivotal movement relative thereto between a first position in which said first and second longitudinal sections may be separated in said first lateral direction, and a second position in which said retaining clip means engage said first and second longitudinal sections along overlapping portions thereof and prevent their separation in said first lateral direction.

14. Motion restraining knee brace apparatus comprising:
    a duality of elongated thigh support members positionable along opposite lateral sides of a thigh portion of a human leg;
    a duality of elongated calf support members positionable along opposite lateral sides of a calf portion of the leg, each of said thigh support members and said calf support members having:
        a first longitudinal section having opening means formed therein,
        a second longitudinal section having protruberance means formed thereon for releasable insertion, in a first lateral direction, into a selected portion of said opening means to selectively vary the length of the support member and to longitudinally and pivotally lock said first and second longitudinal sections thereof, and
        a retaining member carried by one of said first and second longitudinal sections for movement between a first position in which said first and second longitudinal sections may be separated in said first lateral direction, and a second position in which said retaining member prevents their separation in said first lateral direction;
    hinge means, positionable adjacent a knee portion of the leg, for pivotally interconnecting the thigh and calf support members positionable on the same lateral side of the leg, said hinge means being selectively adjustment to limit the relative pivotal movement of the interconnected thigh and calf support members to a predetermined angular range; and
    connecting means for operatively securing said thigh and calf support members to the leg,
        said opening means including a longitudinally spaced series of openings formed through said first longitudinal section,
        said protruberance means including a longitudinally spaced duality of lateral projections carried by said second longitudinal section and adapted to be releasably inserted in a selected adjacent pair of said openings, and
        said retaining means including a clip member pivotally carried by one of said first and second longitudinal sections and, when in said second position, adapted to engage to each of said first and second longitudinal sections along overlapping portions thereof.

15. The motion restraining knee brace apparatus of claim 14 wherein:
said clip member has a generally U-shaped body portion, and a support arm portion extending from said body portion and pivotally connected to said second longitudinal section.

16. The motion restraining knee brace apparatus of claim 15 wherein:
said first longitudinal section has an inner end notch, and
said support arm portion is pivotally connected to said second longitudinal section by a connecting member having an outwardly projecting head portion adapted to be received in said end notch or any of said openings.

17. Adjustable hinge apparatus for pivotally interconnecting first and second members and selectively limiting their relative pivotal motion to a predetermined angular range, comprising:
base means;
a duality of stop members each carried by said base means for arcuate translational movement relative thereto into a selected one of a series of positions thereon;
a dial member carried by said base means for rotational movement relative thereto and relative to said duality of stop members; and
cooperating means on said base means, said duality of stop members and said dial member for sequentially:
causing said dial member, during a first rotational movement of said dial member relative to said base means and relative to said duality of stop members, to engage a selected one of said first duality of stop members and carry it away from an initial position thereof on said base means,
permitting the dial member-moved stop member to be manually moved out of carriable engagement with said dial member to a second position on said base means, and
locking the manually moved stop member on said base means in said second position in response to a second rotational movement of said dial member relative to said base means and said selected one of said duality of stop members;
first attachment means for anchoring one of said first and second members to said base means; and
second attachment means for connecting the other of said first and second members to said base means for pivotal motion relative thereto between and into motion limiting engagement with said duality of stop members.

18. Motion restraining knee brace apparatus comprising:
a first duality of elongated leg support members respectively positionable to expand lengthwise along one lateral side of thigh and calf portions of a human leg;
a second duality of elongated leg support members respectively positionable to extend lengthwise along the opposite lateral side of said thigh and calf portion of the leg;
connecting means for operatively securing said leg support members to the leg;
first hinge means, positionable adjacent a knee portion of the leg, for pivotally interconnecting facing end portions of said first duality of leg support members; and
second hinge means, positionable adjacent said knee portion of the leg, for pivotally interconnecting facing end portions of said second duality of leg support members, each of said first and second hinge means being adjustable to selectively limit the relative pivotal movement of its associated duality of leg support members to a predetermined angular range extending between selectively variable extension and flexion limit angles, each of said first and second hinge means including:
base means,
a duality of stop members each carried by said base means for arcuate translational movement relative thereto into a selected one of a series of positions thereon,
a dial member carried by said base means for rotational movement relative thereto and relative to said duality of stop members, and
cooperating means on said base means, said duality of stop members and said dial member for sequentially:
causing said dial member, during a first rotational movement thereof relative to said base means and relative to said duality of stop members, to engage a selected one of said duality of stop members and carry it away from an initial position thereof on said base means,
permitting the dial member-moved stop member to be manually moved out of carriable engagement with said dial member to a second position on said base means, and
locking the manually moved stop member on said base means in said second position in response to a second rotational movement of said dial member relative to said base means and said selected one of said duality of stop members;
first attachment means for anchoring an end portion of one said leg support members in each of said first and second dualities thereof to the base means of its associated hinge means; and
second attachment means for connecting an end portion of the other said leg support members in each of said first and second dualities thereof to the base means of its associated hinge means for pivotal motion relative thereto between and into motion-limiting engagement with the first and second stop members carried thereby.

19. Motion restraining knee brace apparatus comprising:
a first duality of elongated leg support members respectively positionable to extend lengthwise along one lateral side of thigh and calf portions of a human leg;
a second duality of elongated leg support members respectively positionable to extend lengthwise along the opposite lateral side of said thigh and calf portion of the leg;
connecting means for operatively securing said leg support members to the leg;
first hinge means, positionable adjacent a knee portion of the leg, for pivotally interconnecting facing end portions of said first duality of leg support members; and
second hinge means, positionable adjacent said knee portion of the leg, for pivotally interconnecting facing end portions of said second duality of leg support members, each of said first and second hinge means being adjustable to selectively limit the relative pivotal movement of its associated duality of leg support members to a predetermined angular range extending between electively variable extension and flexion limit angles, each of said first and second hinge means including:

base means, a duality of stop members each carried by said base means for translational movement relative thereto into a selected one of a series of positions thereon, an adjustment member carried by said base means for movement relative thereto, and cooperating means on said base means, said duality of stop members and said adjustment member for sequentially:

causing said adjustment member, during a first movement thereof relative to said base means, to engage a selected one of said duality of stop members and move it away from an initial position thereof on said base means, permitting the adjustment member-moved stop member to be manually moved to a second position on said base means, and locking the manually moved stop member on said base means in said second position in response to a second movement of said adjustment member relative to said base means;

first attachment means for anchoring an end portion of one of said leg support members in each of said first and second dualities thereof to the base means of its associated hinge means; and second attachment means for connecting an end portion of the other said leg support members in each of said first and second dualities thereof to the base means of its associated hinge means for pivotal motion relative thereto between and into motion-limiting engagement with the first and second stop members carried thereby, said base means including a pair of base members each having formed therein an arcuate extension slot having a circumferentially spaced series of notches formed along a side surface thereof, and an arcuate flexion slot having a circumferentially spaced series of notches formed along a side surface thereof, said duality of stop members comprising an extension pivot stop member and a flexion pivot stop member each sandwiched between said base plates, said adjustment means including a dial member carried by one of said base members for rotation relative thereto, and said cooperating means including:

a locking element secured to said extension pivot stop member and having opposite end portions carried in said extension slots and adapted to enter and be circumferentially locked in selected notches thereof, a locking element secured to said flexion pivot stop member and having opposite end portions carried in said flexion slots and adapted to enter and be circumferentially locked in selected notches thereof, an annular flange on said dial member having an internal side surface adapted to engage said locking elements and captively retain them in notches of said extension and flexion slots, a depression formed in said internal side surface of said annular flange and adapted to radially receive an outer end of one of said locking elements, and a spring member carried by said dial member, said spring member being adapted to engage and resiliently urge said outer end of one of said locking elements into said depression and resiliently retain it in said depression for rotational movement with said dial member.

20. The motion restraining knee brace apparatus of claim 19 further comprising:

a series of observation holes formed in said dial member and through which the positions of said locking elements relative to said base members may be visually observed.

21. The motion restraining knee brace apparatus of claim 19 further comprising:

locking means for selectively locking said dial member against rotation relative to said base members.

22. The motion restraining knee brace apparatus of claim 21 wherein said locking means include:

a pair of aligned locking slots formed in said base members, a locking member sandwiched between said base members and movable relative thereto, said locking member having a locking element carried at opposite ends in said locking slots so that said locking member may be moved between first and second positions relative to said base members, said locking element of said locking member having an outer end projecting outwardly from the base member upon which said dial member is mounted, an external notch formed in the periphery of said dial member and defined by outwardly projecting side portions of said dial member, said external notch being adapted to receive said projecting outer end of said locking element on said locking member, said projecting outer end of said locking element on said locking member, when received in said external notch with said locking member held in said first position, cooperating with said side portions to prevent rotation of said dial member relative to said base members, spring means for resiliently biasing said locking member toward said first position and permitting said locking member to be moved to said second position by engagement of either of said outwardly projecting side portions with said projecting outer end of said locking element on said locking member to thereby permit said outwardly projecting side portions to be rotated past said projecting outer end of said locking element on said locking member against the biasing force of said spring means, and holding means for selectively holding said projecting outer end of said locking member locking element in said external notch on said dial member.

23. The motion restraining knee brace apparats of claim 22 wherein:

said holding means include a pair of aligned openings formed through said base plates and adapted to receive a blocking member which blocks movement of said locking member from said first position toward said second position.

24. Motion restraining knee brace apparatus comprising:
- an elongated thigh support member positionable along a lateral side of a thigh portion of a human leg;
- an elongated calf support member positionable along said lateral side of a calf portion of the leg;
- connecting means for operatively securing said thigh and calf support members to the leg; and
- hinge means, positionable adjacent a knee portion of the leg, pivotally interconnecting facing end portions of said thigh and calf support members, said hinge means being selectively adjustable to limit the relative pivotal movement of the interconnected thigh and calf support members to a predetermined angular range extending between an extension limit angle and a flexion limit angle, said hinge means including:
- base means having arcuate track means formed therein, said track means having a first radial portion, and a second radial portion having a circumferentially spaced series of radially extending notches formed therein,
- first and second circumferentially spaced stop members having locking portions carried in said track means for circumferential movement around said first radial portion thereof, said locking portion being radially movable into selected ones of said notches to thereby circumferentially lock said first and second stop members in a desired relative orientation on said base means,
- first attachment means for anchoring one of said facing end portions of said thigh and calf support members to said base means,
- second attachment means for connecting the other of said facing end portions of said thigh and calf support members to said base means for pivotal motion relative thereto between and into motion limiting engagement with said first and second stop members,
- dial means, carried by said base means for rotation relative thereto, for selectively repositioning said first and second stop members on said base means, said dial means having an arcuate retaining surface adapted to retain said locking portions in first and second ones of said notches, said retaining surface having a depression formed therein and adapted to radially receive either of said locking portions when said depression is rotated into circumferentially alignment with the locking portion, and to carry the received locking portion around said first radial portion of said track means into circumferentially alignment with a third one of said notches upon further rotation of said dial means so that the stop member associated with the received locking portion may be manually moved to position the received locking member in said third one of said notches and the dial means further rotated to cause said retaining surface to retain the received locking portion in said third one of said notches, and
- spring means, carried by said dial means for rotation therewith, for engaging a selected one of said locking portions and resiliently urging it outwardly from one of said notches and into said depression formed in said retaining surface.

25. The motion restraining knee brace apparatus of claim 24 further comprising:
- a series of observation holes formed in said dial means and through which the positions of said locking portions of said stop members relative to said base means may be visually observed.

26. The motion restraining knee brace apparatus of claim 24 further comprising:
- locking means for selectively locking said dial means against rotation to said base means.

27. The motion restraining knee brace apparatus of claim 26 wherein:
- said locking means include a locking member carried by said base means for movement relative thereto between a first position and a second position, spring means for biasing said locking member toward said first position, cooperating means on said locking member and said dial means for locking said dial means when said locking member is held in said first position, and holding means for selectively holding said locking member in said first position.

28. Motion restraining knee brace apparatus comprising:
- first and second thigh support members positionable along opposite lateral sides of a thigh portion of a human leg;
- first and second calf support members positionable along opposite lateral sides of a calf portion of the leg;
- first hinge means, positionable adjacent a knee area of the leg, for pivotally interconnecting said first thigh and calf support members on one lateral side of the leg;
- second hinge means, positionable adjacent a knee area of the leg, for pivotally interconnecting said second thigh and calf support members on the opposite lateral side of the leg;
- first connecting means for operatively securing said first and second thigh support members to the leg;
- second connecting means for operatively securing said first and second calf support members;
- connector means secured to said thigh and calf support members for movement therewith; and
- elongated flexible restraining means slidable looped through said connector means to form a continuous, flexible motion restraining network positioned entirely behind said leg, said network having a criss-crossed central portion positionable to extend longitudinally along a posterior portion of the leg extending from above the knee to below the knee, and first and second end portions adapted to extend transversely along opposite ends of said posterior portion, said central and end portions of said network being adapted to be progressively tightened against the leg during extension thereof, and to be maintained in essentially identical tension.

29. The motion restraining knee brace apparatus of claim 28 wherein:
- said connector means include a first pair of connector members having openings therethrough and being secured to said first and second thigh support members, and a second pair of connector members having openings therethrough and being secured to said first and second calf support members.

30. The motion restraining knee brace apparatus of claim 29 wherein:
- said elongated flexible restraining means comprises a pair of restraining straps and adjustable buckle means for intersecuring free end portions of said restraining straps.

31. Motion restraining knee brace apparatus comprising:
a duality of elongated, essentially rigid thigh support members positionable along opposite lateral sides of a thigh portion of a human leg;
a duality of elongated, essentially rigid calf support members positionable along opposite lateral sides of a calf portion of the leg;
hinge means, positionable adjacent a knee portion of the leg, for pivotally interconnecting the thigh and calf support members positionable on the same lateral side of the leg, said hinge means being selectively adjustable to limit the relative pivotal movement of the interconnected thigh and calf support members to a predetermined angular range extending between a leg extension limit angle and a leg flexion limit angle;
connecting means for operatively securing said thigh and calf support members to the leg; and
flexible restraining means, carried by said thigh and calf support members, for inhibiting extension of the leg beyond said extension limit angle, said flexible restraining means being positionable entirely posteriorly of the leg, configured to longitudinally span and exert pressure against a posterior longitudinal portion of the leg extending from longitudinally above the knee to longitudinally below the knee and to laterally span and exert pressure against opposite ends of said posterior longitudinal portion, and being operative to be progressively and uniformly loosened along said posterior longitudinal portion by said thigh and calf support members as the leg is flexed toward said leg flexion limit angle, and to be progressively and uniformly tightened against said posterior longitudinal portion by said thigh and calf support members as the leg is extended toward side leg extension limit angle.

32. The motion restraining knee brace apparatus of claim 31 wherein:
said apparatus further comprises first and second pairs of connector members respectively secured to said thigh support members and to said calf support members, and
said flexible restraining means include restraining strap means slidably looped through said first and second pairs of connector members to form a generally hourglass-shaped restraining strap network.

33. The motion restraining knee brace apparatus of claim 32 wherein:
said restraining strap means include first and second restraining straps, and buckle means for adjustably intersecuring adjacent free end portions of said first and second restraining straps.

34. The motion restraining knee brace of claim 31 wherein said connecting means include:
first strap means interconnectable between said thigh support members and adapted to generally encircle said thigh portion of the leg, and
second strap means interconnectable between said calf support members and adapted to generally encircle said calf portion of the leg,
said first and second strap means each having anterior and posterior portions whose length are independently adjustable to thereby precisely position and hold said thigh and calf support members in desired anterior-posterior orientations along said thigh and calf portions of the leg.

35. The motion restraining knee brace apparatus of claim 34 wherein:
said apparatus further comprises first strap connector means carried by one of said thigh support members, and second strap connector means carried by one of said calf support members,
said first strap means include a first connection strap having a central portion anchored to the other of said thigh support members, said first connection strap having a pair of free end portions with outer ends which may be passed through said first strap connector means, and first tightening means for adjustably tightening each of said free end portions against the leg, and
said second strap means include a second connection strap having a central portion anchored to the other of said calf support members, said second connection strap having a pair of free end portions with the outer ends which may be passed through said second strap connector means, and second tightening means for adjustably tightening each of said pair of free end portions of said second connection strap against the leg.

36. The motion restraining knee brace apparatus of claim 35 wherein:
said first strap connector means include a first pair of connector members having openings formed therethrough,
said second strap connector means include a second pair of connector members having openings formed therethrough, and
said first and second tightening means include cooperating hook and pile surfaces formed on said outer ends and said free end portions of said first and second connection straps.

37. The motion restraining knee brace apparatus of claim 36 wherein:
said first pair of connector members are positioned adjacent a longitudinally outer end of said one of said thigh support members, and
said second pair of connector members are positioned adjacent a longitudinally outer end of said one of said calf support members.

38. The motion restraining knee brace apparatus of claim 37 wherein said connecting means further comprise:
adjustably tightenable first anterior strap means interconnected between said thigh support members and positioned between said first pair of connector members and said first and second hinge means, and
adjustably tightenable second anterior strap means interconnected between said calf support members and positioned between said second pair of connector members and said first and second hinge means.

* * * * *